US008637316B2

United States Patent
Migiwa et al.

(10) Patent No.: US 8,637,316 B2
(45) Date of Patent: Jan. 28, 2014

(54) GLYCININ SIGNAL SEQUENCE FOR PRODUCING SECRETED PROTEINS IN PLANTS

(75) Inventors: Keiko Migiwa, Toyonaka (JP); Yutaka Matsushima, Kobe (JP); Akitsu Nagasawa, Kobe (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 485 days.

(21) Appl. No.: 12/503,615

(22) Filed: Jul. 15, 2009

(65) Prior Publication Data

US 2010/0319090 A1 Dec. 16, 2010

(30) Foreign Application Priority Data

Jul. 16, 2008 (JP) ................ 2008-184479

(51) Int. Cl.
  *C12N 15/82* (2006.01)
  *A01H 5/00* (2006.01)
  *C07H 21/04* (2006.01)
(52) U.S. Cl.
  USPC ........... 435/468; 435/419; 800/278; 800/288; 800/295; 800/298; 536/23.1; 536/23.4; 536/23.5; 536/23.6
(58) Field of Classification Search
  None
  See application file for complete search history.

(56) References Cited

U.S. PATENT DOCUMENTS 7,368,628 B2 * 5/2008 Kawagoe et al. ............. 800/278

OTHER PUBLICATIONS

Ding et al. High-level expression of basic fibroblast growth factor in transgenic soybean seeds and characterization of its biological activity. (2006) Biotechnol. lett; vol. 28; pp. 869-875.*
Mi et al. Glycine Max cultivar Nan Nong 87-C38 glycinin gy1 precursor, gene, promoter region, 5' UTR and partial cds. (2005) GenBank Accession AY649096; p. 1.*
Dockal et al. The three recombinant domains of human serum albumin. (1999) JBC; vol. 274; pp. 29303-29310.*
Worley et al. Engineering in vivo instability of firefly luciferase and *Escherichia coli* B-glucuronidase in higher plants using recognition elements from the ubiquitin pathway. (1998) PMB; vol. 37; pp. 337-347.*
Varshaysky, A. The N-end Rule. (1995) Cold Spring Harbor Symp. Quant. Biol; pp. 461-478.*

* cited by examiner

*Primary Examiner* — Cathy Kingdon Worley
(74) *Attorney, Agent, or Firm* — Birch, Stewart, Kolasch & Birch, LLP

(57) ABSTRACT

The present invention relates to a method for producing a heterologous protein secreted out of a plant cell comprising introducing into a plant cell genome a DNA encoding an amino acid sequence that comprises a glycinin signal sequence for endoplasmic reticulum transport and an amino acid sequence of a heterologous protein, wherein the signal sequence is directly fused to the amino acid sequence of the heterologous protein or one or two amino acids are inserted between the signal sequence and the amino acid sequence of the heterologous protein; and expressing the DNA.

9 Claims, 5 Drawing Sheets

SEQUENCE LISTING

```
<160> NUMBER OF SEQ ID NOS: 54

<210> SEQ ID NO 1
<211> LENGTH: 19
<212> TYPE: PRT
<213> ORGANISM: Glycine max

<400> SEQUENCE: 1

Met Ala Lys Leu Val Phe Ser Leu Cys Phe Leu Leu Phe Ser Gly Cys
1               5                   10                  15

Cys Phe Ala

<210> SEQ ID NO 2
<211> LENGTH: 18
<212> TYPE: PRT
<213> ORGANISM: Glycine max

<400> SEQUENCE: 2

Met Ala Lys Leu Val Leu Ser Leu Cys Phe Leu Leu Phe Ser Gly Cys
1               5                   10                  15

Phe Ala

<210> SEQ ID NO 3
<211> LENGTH: 19
<212> TYPE: PRT
<213> ORGANISM: Glycine max

<400> SEQUENCE: 3

Met Ala Lys Leu Val Leu Ser Leu Cys Phe Leu Leu Phe Ser Gly Cys
1               5                   10                  15

Cys Phe Ala

<210> SEQ ID NO 4
<211> LENGTH: 23
<212> TYPE: PRT
<213> ORGANISM: Glycine max

<400> SEQUENCE: 4

Met Gly Lys Pro Phe Thr Leu Ser Leu Ser Ser Leu Cys Leu Leu Leu
1               5                   10                  15

Leu Ser Ser Ala Cys Phe Ala
            20
```

<210> SEQ ID NO 5
<211> LENGTH: 24
<212> TYPE: PRT
<213> ORGANISM: Glycine max

<400> SEQUENCE: 5

Met Gly Lys Pro Phe Phe Thr Leu Ser Leu Ser Ser Leu Cys Leu Leu
1               5                   10                  15

Leu Leu Ser Ser Ala Cys Phe Ala
            20

<210> SEQ ID NO 6
<211> LENGTH: 720
<212> TYPE: DNA
<213> ORGANISM: Artificial Sequence
<220> FEATURE:
<223> OTHER INFORMATION: synthesized DNA

<400> SEQUENCE: 6

| | |
|---|---|
| atggtgagca agggcgagga gctgttcacc ggggtggtgc ccatcctggt cgagctggac | 60 |
| ggcgacgtga acggccacaa gttcagcgtg tccggcgagg gcgagggcga tgccacctac | 120 |
| ggcaagctga ccctgaagtt catctgcacc accggcaagc tgcccgtgcc ctggcccacc | 180 |
| ctcgtgacca ccttcaccta cggcgtgcag tgcttcagcc gctaccccga ccacatgaag | 240 |
| cagcacgact tcttcaagtc cgccatgccc gaaggctacg tccaggagcg caccatcttc | 300 |
| ttcaaggacg acggcaacta caagacccgc gccgaggtga agttcgaggg cgacaccctg | 360 |
| gtgaaccgca tcgagctgaa gggcatcgac ttcaaggagg acggcaacat cctggggcac | 420 |
| aagctggagt acaactacaa cagccacaac gtctatatca tggccgacaa gcagaagaac | 480 |
| ggcatcaagg tgaacttcaa gatccgccac aacatcgagg acggcagcgt gcagctcgcc | 540 |
| gaccactacc agcagaacac ccccatcggc gacggccccg tgctgctgcc cgacaaccac | 600 |
| tacctgagca cccagtccgc cctgagcaaa gaccccaacg agaagcgcga tcacatggtc | 660 |
| ctgctggagt tcgtgaccgc cgccgggatc actcacggca tggacgagct gtacaagtaa | 720 |

<210> SEQ ID NO 7
<211> LENGTH: 33
<212> TYPE: DNA
<213> ORGANISM: Artificial Sequence
<220> FEATURE:
<223> OTHER INFORMATION: Synthetic primer

<400> SEQUENCE: 7
gctagcgtga gcaagggcga ggagctgttc acc                              33

<210> SEQ ID NO 8
<211> LENGTH: 33
<212> TYPE: DNA
<213> ORGANISM: Artificial Sequence
<220> FEATURE:
<223> OTHER INFORMATION: Synthetic primer

<400> SEQUENCE: 8
gagctcttac ttgtacagct cgtccatgcc gtg                              33

<210> SEQ ID NO 9
<211> LENGTH: 60
<212> TYPE: DNA
<213> ORGANISM: Artificial Sequence
<220> FEATURE:
<223> OTHER INFORMATION: synthesized oligonucleotide

<400> SEQUENCE: 9
gatccatggc caagctagtt ttttcccttt gttttctgct tttcagtggc tgctgcttcg    60

<210> SEQ ID NO 10
<211> LENGTH: 60
<212> TYPE: DNA
<213> ORGANISM: Artificial Sequence
<220> FEATURE:
<223> OTHER INFORMATION: synthesized oligonucleotide

<400> SEQUENCE: 10
ctagcgaagc agcagccact gaaaagcaga aacaaaggg aaaaaactag cttggccatg    60

<210> SEQ ID NO 11
<211> LENGTH: 789
<212> TYPE: DNA
<213> ORGANISM: Artificial Sequence
<220> FEATURE:
<223> OTHER INFORMATION: DNA encoding chemically synthesized fused
      protein

<400> SEQUENCE: 11
ggatccatgg ccaagctagt tttttccctt tgttttctgc ttttcagtgg ctgctgcttc     60
gctagcgtga gcaagggcga ggagctgttc accggggtgg tgcccatcct ggtcgagctg    120
gacggcgacg tgaacggcca agttcagc gtgtccggcg agggcgaggg cgatgccacc     180
tacggcaagc tgacccctgaa gttcatctgc accaccggca agctgcccgt gccctggccc    240
accctcgtga ccaccttcac ctacggcgtg cagtgcttca gccgctaccc cgaccacatg    300
aagcagcacg acttcttcaa gtccgccatg cccgaaggct acgtccagga gcgcaccatc    360
ttcttcaagg acgacggcaa ctacaagacc cgcgccgagg tgaagttcga gggcgacacc    420
ctggtgaacc gcatcgagct gaagggcatc gacttcaagg aggacggcaa catcctgggg    480
cacaagctgg agtacaacta caacagccac aacgtctata tcatggccga caagcagaag    540
aacggcatca aggtgaactt caagatccgc cacaacatcg aggacggcag cgtgcagctc    600
gccgaccact accagcagaa cacccccatc ggcgacggcc ccgtgctgct gcccgacaac    660
cactacctga gcacccagtc cgccctgagc aaagacccca acgagaagcg cgatcacatg    720
gtcctgctgg agttcgtgac cgccgccggg atcactcacg gcatggacga gctgtacaag    780
taagagctc                                                           789

<210> SEQ ID NO 12
<211> LENGTH: 33
<212> TYPE: DNA
<213> ORGANISM: Artificial Sequence
<220> FEATURE:
<223> OTHER INFORMATION: forward synthetic primer

<400> SEQUENCE: 12
gagtcaggat ccatggccaa gctagttttt tcc                                  33

<210> SEQ ID NO 13
<211> LENGTH: 24
<212> TYPE: DNA
<213> ORGANISM: Artificial Sequence
<220> FEATURE:
<223> OTHER INFORMATION: modified reverse synthetic primer

<400> SEQUENCE: 13
cttgctcaca gcgaagcagc agcc                                            24

<210> SEQ ID NO 14
<211> LENGTH: 27
<212> TYPE: DNA
<213> ORGANISM: Artificial Sequence
<220> FEATURE:
<223> OTHER INFORMATION: modified reverse synthetic primer

<400> SEQUENCE: 14
cttgctcacc atagcgaagc agcagcc                                          27

<210> SEQ ID NO 15
<211> LENGTH: 24
<212> TYPE: DNA
<213> ORGANISM: Artificial Sequence
<220> FEATURE:
<223> OTHER INFORMATION: modified reverse synthetic primer

<400> SEQUENCE: 15
cttgctcaca gcagcgaagc agca                                             24

<210> SEQ ID NO 16
<211> LENGTH: 33
<212> TYPE: DNA
<213> ORGANISM: Artificial Sequence
<220> FEATURE:
<223> OTHER INFORMATION: reverse prmer

<400> SEQUENCE: 16
gttcgagagc tcttacttgt acagctcgtc cat                                   33

<210> SEQ ID NO 17
<211> LENGTH: 24
<212> TYPE: DNA
<213> ORGANISM: Artificial Sequence
<220> FEATURE:
<223> OTHER INFORMATION: modified reverse synthetic primer

<400> SEQUENCE: 17
cttgctcacg ccagcgaagc agca                                             24

<210> SEQ ID NO 18
<211> LENGTH: 27
<212> TYPE: DNA
<213> ORGANISM: Artificial Sequence
<220> FEATURE:
<223> OTHER INFORMATION: modifed reverse synthetic primer

<400> SEQUENCE: 18
cttgctcaca agagcgaagc agcagcc                                          27

<210> SEQ ID NO 19
<211> LENGTH: 27
<212> TYPE: DNA
<213> ORGANISM: Artificial Sequence
<220> FEATURE:
<223> OTHER INFORMATION: modified reverse synthetic primer

<400> SEQUENCE: 19
cttgctcacg atagcgaagc agcagcc                                          27

<210> SEQ ID NO 20
<211> LENGTH: 27
<212> TYPE: DNA
<213> ORGANISM: Artificial Sequence
<220> FEATURE:
<223> OTHER INFORMATION: modified reverse synthetic primer

```
<400> SEQUENCE: 20
cttgctcaca acagcgaagc agcagcc                                              27

<210> SEQ ID NO 21
<211> LENGTH: 24
<212> TYPE: DNA
<213> ORGANISM: Artificial Sequence
<220> FEATURE:
<223> OTHER INFORMATION: modified reverse synthetic primer

<400> SEQUENCE: 21
cttgctcacg ggagcgaagc agca                                                 24

<210> SEQ ID NO 22
<211> LENGTH: 27
<212> TYPE: DNA
<213> ORGANISM: Artificial Sequence
<220> FEATURE:
<223> OTHER INFORMATION: modified reverse synthetic primer

<400> SEQUENCE: 22
cttgctcaca gtagcgaagc agcagcc                                              27

<210> SEQ ID NO 23
<211> LENGTH: 24
<212> TYPE: DNA
<213> ORGANISM: Artificial Sequence
<220> FEATURE:
<223> OTHER INFORMATION: modified reverse synthetic primer

<400> SEQUENCE: 23
cttgctcacg tgagcgaagc agca                                                 24

<210> SEQ ID NO 24
<211> LENGTH: 27
<212> TYPE: DNA
<213> ORGANISM: Artificial Sequence
<220> FEATURE:
<223> OTHER INFORMATION: modified reverse synthetic primer

<400> SEQUENCE: 24
cttgctcact tgagcgaagc agcagcc                                              27

<210> SEQ ID NO 25
<211> LENGTH: 27
<212> TYPE: DNA
<213> ORGANISM: Artificial Sequence
<220> FEATURE:
<223> OTHER INFORMATION: modified reverse synthetic primer

<400> SEQUENCE: 25
cttgctcact tcagcgaagc agcagcc                                              27

<210> SEQ ID NO 26
<211> LENGTH: 27
<212> TYPE: DNA
<213> ORGANISM: Artificial Sequence
<220> FEATURE:
<223> OTHER INFORMATION: modified reverse synthetic primer

<400> SEQUENCE: 26
cttgctcacg ttagcgaagc agcagcc                                              27

<210> SEQ ID NO 27
<211> LENGTH: 27
<212> TYPE: DNA
```

```
<213> ORGANISM: Artificial Sequence
<220> FEATURE:
<223> OTHER INFORMATION: modified reverse synthetic primer

<400> SEQUENCE: 27
cttgctcaca tcagcgaagc agcagcc                                        27

<210> SEQ ID NO 28
<211> LENGTH: 27
<212> TYPE: DNA
<213> ORGANISM: Artificial Sequence
<220> FEATURE:
<223> OTHER INFORMATION: modified reverse synthetic primer

<400> SEQUENCE: 28
cttgctcacc ttagcgaagc agcagcc                                        27

<210> SEQ ID NO 29
<211> LENGTH: 24
<212> TYPE: DNA
<213> ORGANISM: Artificial Sequence
<220> FEATURE:
<223> OTHER INFORMATION: modified reverse synthetic primer

<400> SEQUENCE: 29
cttgctcacg caagcgaagc agca                                           24

<210> SEQ ID NO 30
<211> LENGTH: 27
<212> TYPE: DNA
<213> ORGANISM: Artificial Sequence
<220> FEATURE:
<223> OTHER INFORMATION: modified reverse synthetic primer

<400> SEQUENCE: 30
cttgctcact ctagcgaagc agcagcc                                        27

<210> SEQ ID NO 31
<211> LENGTH: 27
<212> TYPE: DNA
<213> ORGANISM: Artificial Sequence
<220> FEATURE:
<223> OTHER INFORMATION: modified reverse synthetic primer

<400> SEQUENCE: 31
cttgctcacg taagcgaagc agcagcc                                        27

<210> SEQ ID NO 32
<211> LENGTH: 24
<212> TYPE: DNA
<213> ORGANISM: Artificial Sequence
<220> FEATURE:
<223> OTHER INFORMATION: modified reverse synthetic primer

<400> SEQUENCE: 32
cttgctcacc caagcgaagc agca                                           24

<210> SEQ ID NO 33
<211> LENGTH: 27
<212> TYPE: DNA
<213> ORGANISM: Artificial Sequence
<220> FEATURE:
<223> OTHER INFORMATION: modified reverse synthetic primer

<400> SEQUENCE: 33
cttgctcacg aaagcgaagc agcagcc                                        27
```

-continued

<210> SEQ ID NO 34
<211> LENGTH: 24
<212> TYPE: DNA
<213> ORGANISM: Artificial Sequence
<220> FEATURE:
<223> OTHER INFORMATION: modified reverse synthetic primer

<400> SEQUENCE: 34
cttgctcacg ccgctagcga agca                                          24

<210> SEQ ID NO 35
<211> LENGTH: 27
<212> TYPE: DNA
<213> ORGANISM: Artificial Sequence
<220> FEATURE:
<223> OTHER INFORMATION: modified reverse synthetic primer

<400> SEQUENCE: 35
cttgctcaca gcgctagcga agcagca                                       27

<210> SEQ ID NO 36
<211> LENGTH: 24
<212> TYPE: DNA
<213> ORGANISM: Artificial Sequence
<220> FEATURE:
<223> OTHER INFORMATION: modified reverse synthetic primer

<400> SEQUENCE: 36
cttgctcacg ccagcagcga agca                                          24

<210> SEQ ID NO 37
<211> LENGTH: 1620
<212> TYPE: DNA
<213> ORGANISM: Artificial Sequence
<220> FEATURE:
<223> OTHER INFORMATION: synthesized DNA

<400> SEQUENCE: 37
ggatccatgg ctccaactgc aactcttgct aacggtgata ccattactgg acttaacgct      60
attatcaatg aggcattcct cggtattcct tttgctgagc cacctgttgg taaccttaga     120
ttcaaggacc cagttcctta ctccggatca cttgatggtc agaagtttac ttcttacgga     180
ccatcctgca tgcaacagaa tccagaaggt acctatgaag agaacctccc aaaggctgca     240
cttgatcttg tgatgcagtc caaagttttc gaggctgtgt ctccttcatc cgaggactgt     300
ctcactatta atgttgtgag gccacctgga accaaggctg gtgcaaacct tccagttatg     360
ctttggatct ttggtggagg tttcgaggtt ggtggaactt caacttttcc tccagctcaa     420
atgatcacta gtctattgc tatgggtaaa ccaatcattc atgtttcagt gaattaccgt     480
gtgtcttcat ggggattcct cgcaggtgat gagattaagg ctgaaggttc agctaacgct     540
ggacttaaag accagagact tggtatgcaa tgggttgcag ataatattgc tgcttttgga     600
ggtgacccta ccaaggtgac tatcttcgga gagtccgcag gttctatgtc tgttatgtgt     660
cacattcttt ggaacgatgg agacaatact tataagggta aaccactctt cagagctgga     720
attatgcaat ctggtgctat ggtgccttca gacgcagttg atggaatcta cggtaacgag     780 attttgatc ttcttgcttc caatgctgga tgtggttctg catccgataa gctcgcttgc     840
cttaggggtg tgtcctcaga cacacttgaa gatgctacta caataccccc aggattcctc     900
gcatattcat ctcttagact ttcataccct cctaggccag acggtgttaa cattacagat     960
gacatgtatg ctcttgtgag agagggtaaa tatgctaata tccctgttat tattggagat    1020

```
cagaacgacg aaggtacttt cttcggaaca tcctcactca atgtgactac cgacgctcag    1080
gcaagagagt actttaagca atctttcgtt catgcttcag atgcagaaat tgacactctt    1140
atgactgctt atccaggtga tattactcaa ggctcccctt ttgacacagg cattcttaac    1200
gctctcactc cacaattcaa gaggatttca gcagttcttg gcgatcttgg ttttacccctc   1260 gctagacgtt atttccttaa tcattacact ggtggaacaa agtattcttt cctttcaaaa    1320
cagctttccg gtctcccagt gcttggaact ttccactcaa acgacatcgt tttccaggat    1380
tatcttctcg gttccggttc tcttatttat aataacgctt tcattgcatt cgctaccgac    1440
cttgatccaa atactgctgg actccttgtt aagtggcctg aatacacatc tcttcccaa     1500 agtggtaaca accttatgat gatcaatgct ctcggtcttt atactggtaa agacaacttc    1560
agaaccgcag atacgatgc tcttttctct aatcctccat cattcttcgt gtgagagctc     1620

<210> SEQ ID NO 38
<211> LENGTH: 30
<212> TYPE: DNA
<213> ORGANISM: Artificial Sequence
<220> FEATURE:
<223> OTHER INFORMATION: Synthetic primer

<400> SEQUENCE: 38
gctagcgctc caactgcaac tcttgctaac                                         30

<210> SEQ ID NO 39
<211> LENGTH: 34
<212> TYPE: DNA
<213> ORGANISM: Artificial Sequence
<220> FEATURE:
<223> OTHER INFORMATION: Synthetic primer

<400> SEQUENCE: 39
gagctctcac acgaagaatg atggaggatt agag                                    34

<210> SEQ ID NO 40
<211> LENGTH: 1677
<212> TYPE: DNA
<213> ORGANISM: Artificial Sequence
<220> FEATURE:
<223> OTHER INFORMATION: DNA encoding a chemically synthesized fused
      protein

<400> SEQUENCE: 40
ggatccatgg ccaagctagt ttttccctt tgttttctgc ttttcagtgg ctgctgcttc       60
gctagcgctc caactgcaac tcttgctaac ggtgatacca ttactggact taacgctatt     120
atcaatgagg cattcctcgg tattccttt gctgagccac tgttggtaa ccttagattc       180 aaggacccag ttccttactc cggatcactt gatggtcaga agtttacttc ttacggacca     240
tcctgcatgc aacagaatcc agaaggtacc tatgaagaga acctcccaaa ggctgcactt     300
gatcttgtga tgcagtccaa agttttcgag gctgtgtctc cttcatccga ggactgtctc     360
actattaatg ttgtgaggcc acctggaacc aaggctggtg caaaccttcc agttatgctt     420
tggatctttg gtggaggttt cgaggttggt ggaacttcaa cttttcctcc agctcaaatg     480
atcactaagt ctattgctat gggtaaacca atcattcatg tttcagtgaa ttaccgtgtg     540
tcttcatggg gattcctcgc aggtgatgag attaaggctg aaggttcagc taacgctgga     600
cttaaagacc agagacttgg tatgcaatgg gttgcagata atattgctgc ttttggaggt     660
gaccctacca agtgactat cttcggagag tccgcaggtt ctatgtctgt tatgtgtcac     720
attctttgga acgatggaga caatacttat aagggtaaac cactcttcag agctggaatt     780
```

```
atgcaatctg gtgctatggt gccttcagac gcagttgatg gaatctacgg taacgagatt      840
tttgatcttc ttgcttccaa tgctggatgt ggttctgcat ccgataagct cgcttgcctt      900 agggtgtgt  cctcagacac acttgaagat gctactaaca ataccccagg attcctcgca      960
tattcatctc ttagactttc ataccttcct aggccagacg tgttaacat  tacagatgac     1020 atgtatgctc ttgtgagaga gggtaaatat gctaatatcc ctgttattat tggagatcag     1080
aacgacgaag gtactttctt cggaacatcc tcactcaatg tgactaccga cgctcaggca     1140
agagagtact ttaagcaatc tttcgttcat gcttcagatg cagaaattga cactcttatg     1200
actgcttatc caggtgatat tactcaaggc tccccttttg acacaggcat tcttaacgct     1260
ctcactccac aattcaagag gatttcagca gttcttggcg atcttggttt taccctcgct     1320
agacgttatt tccttaatca ttacactggt ggaacaaagt attctttcct ttcaaaacag     1380
ctttccggtc tcccagtgct tggaactttc cactcaaacg acatcgtttt ccaggattat     1440
cttctcggtt ccggttctct tatttataat aacgctttca ttgcattcgc taccgacctt     1500
gatccaaata ctgctggact ccttgttaag tggcctgaat acacatcctc ttcccaaagt     1560
ggtaacaacc ttatgatgat caatgctctc ggtctttata ctggtaaaga caacttcaga     1620
accgcaggat acgatgctct tttctctaat cctccatcat tcttcgtgtg agagctc       1677
```

<210> SEQ ID NO 41
<211> LENGTH: 22
<212> TYPE: DNA
<213> ORGANISM: Artificial Sequence
<220> FEATURE:
<223> OTHER INFORMATION: Synthetic primer

<400> SEQUENCE: 41
ttgatcttct tgcttccaat gc                                                22

<210> SEQ ID NO 42
<211> LENGTH: 22
<212> TYPE: DNA
<213> ORGANISM: Artificial Sequence
<220> FEATURE:
<223> OTHER INFORMATION: Synthetic primer

<400> SEQUENCE: 42
gtctgaggac acacccctaa gg                                                22

<210> SEQ ID NO 43
<211> LENGTH: 20
<212> TYPE: DNA
<213> ORGANISM: Artificial Sequence
<220> FEATURE:
<223> OTHER INFORMATION: Synthetic primer

<400> SEQUENCE: 43
gaagcagctc gaggatggaa                                                   20

<210> SEQ ID NO 44
<211> LENGTH: 22
<212> TYPE: DNA
<213> ORGANISM: Artificial Sequence
<220> FEATURE:
<223> OTHER INFORMATION: Synthetic primer

<400> SEQUENCE: 44
gacgggttga ctctttctgg at                                                22

```
<210> SEQ ID NO 45
<211> LENGTH: 17
<212> TYPE: DNA
<213> ORGANISM: Artificial Sequence
<220> FEATURE:
<223> OTHER INFORMATION: Synthetic primer

<400> SEQUENCE: 45
gttttcccag tcacgac                                                    17

<210> SEQ ID NO 46
<211> LENGTH: 32
<212> TYPE: DNA
<213> ORGANISM: Artificial Sequence
<220> FEATURE:
<223> OTHER INFORMATION: Synthetic primer

<400> SEQUENCE: 46
ggatccgact gatgagtgtt taaggaccaa tg                                   32

<210> SEQ ID NO 47
<211> LENGTH: 33
<212> TYPE: DNA
<213> ORGANISM: Artificial Sequence
<220> FEATURE:
<223> OTHER INFORMATION: Synthetic primer

<400> SEQUENCE: 47
gagctcaacc aataaataat aataataata atg                                  33

<210> SEQ ID NO 48
<211> LENGTH: 34
<212> TYPE: DNA
<213> ORGANISM: Artificial Sequence
<220> FEATURE:
<223> OTHER INFORMATION: Synthetic primer

<400> SEQUENCE: 48
aagcttcaag tcatgaagaa cctgataaga cgtc                                 34

<210> SEQ ID NO 49
<211> LENGTH: 18
<212> TYPE: DNA
<213> ORGANISM: Artificial Sequence
<220> FEATURE:
<223> OTHER INFORMATION: Synthetic primer

<400> SEQUENCE: 49
gatccgcggc cgcgagct                                                   18

<210> SEQ ID NO 50
<211> LENGTH: 10
<212> TYPE: DNA
<213> ORGANISM: Artificial Sequence
<220> FEATURE:
<223> OTHER INFORMATION: Synthetic primer

<400> SEQUENCE: 50
cgcggccgcg                                                            10

<210> SEQ ID NO 51
<211> LENGTH: 3177
<212> TYPE: DNA
<213> ORGANISM: Artificial Sequence
<220> FEATURE:
<223> OTHER INFORMATION: DNA encoding chemically synthesized fused
      protein
```

<400> SEQUENCE: 51

```
gaattctctc ttataaaaca caaacacaat ttttagattt tatttaaata atcatcaatc      60
gattataatt atttatatat ttttctattt tcaaagaagt aaatcatgag cttttccaac     120
tcaacatcta ttttttttct ctcaacctt ttcacatctt aagtagtctc accctttata     180
tatataactt atttcttacc ttttacatta tgtaactttt atcaccaaaa ccaacaactt     240
taaaatttta ttaaatagac tccacaagta acttgacact cttacattca tcgacattaa     300
ctttatctg ttttataaat attattgtga tataatttaa tcaaataac cacaaacttt      360
cataaaaggt tcttattaag catggcattt aataagcaaa aacaactcaa tcactttcat     420
ataggaggta gcctaagtac gtactcaaaa tgccaacaaa taaaaaaaaa gttgctttaa     480
taatgccaaa acaaattaat aaaacactta caacaccgga ttttttttaa ttaaaatgtg     540
ccatttagga taaatagtta atatttttaa taattattta aaaagccgta tctactaaaa     600
tgatttttat ttggttgaaa atattaatat gtttaaatca acacaatcta tcaaaattaa     660
actaaaaaaa aaataagtgt acgtggttaa cattagtaca gtaatataag aggaaaatga     720
gaaattaaga aattgaaagc gagtctaatt tttaaattat gaacctgcat atataaaagg     780
aaagaaagaa tccaggaaga aaagaaatga aaccatgcat ggtcccctcg tcatcacgag     840
tttctgccat ttgcaataga aacactgaaa caccttttctc tttgtcactt aattgagatg     900
ccgaagccac ctcacaccat gaacttcatg aggtgtagca cccaaggctt ccatagccat     960
gcatactgaa gaatgtctca agctcagcac cctacttctg tgacgtgtcc ctcattcacc    1020
ttcctctctt ccctataaat aaccacgcct caggttctcc gcttcacaac tcaaacattc    1080
tctccattgg tccttaaaca ctcatcagtc ggatccatgg ccaagctagt tttttccctt    1140
tgttttctgc ttttcagtgg ctgctgcttc gctagcgctc caactgcaac tcttgctaac    1200
ggtgatacca ttactggact taacgctatt atcaatgagg cattcctcgg tattcctttt    1260
gctgagccac ctgttggtaa ccttagattc aaggacccag ttccttactc cggatcactt    1320
gatggtcaga agtttacttc ttacggacca tcctgcatgc aacagaatcc agaaggtacc    1380
tatgaagaga acctcccaaa ggctgcactt gatcttgtga tgcagtccaa agttttcgag    1440
gctgtgtctc cttcatccga ggactgtctc actattaatg ttgtgaggcc acctggaacc    1500
aaggctggtg caaaccttcc agttatgctt tggatctttg gtggaggttt cgaggttggt    1560
ggaacttcaa cttttcctcc agctcaaatg atcactaagt ctattgctat gggtaaacca    1620
atcattcatg tttcagtgaa ttaccgtgtg tcttcatggg gattcctcgc aggtgatgag    1680
attaaggctg aaggttcagc taacgctgga cttaaagacc agagacttgg tatgcaatgg    1740
gttgcagata atattgctgc ttttggaggt gaccctacca aggtgactat cttcggagag    1800
tccgcaggtt ctatgtctgt tatgtgtcac attctttgga acgatggaga caatacttat    1860
aagggtaaac cactcttcag agctggaatt atgcaatctg tgctatggt gccttcagac    1920
gcagttgatg gaatctacgg taacgagatt tttgatcttc ttgcttccaa tgctggatgt    1980
ggttctgcat ccgataagct cgcttgcctt aggggtgtgt cctcagacac acttgaagat    2040
gctactaaca ataccccagg attcctcgca tattcatctc ttagactttc ataccttcct    2100
aggccagacg tgttaacat acagatgac atgtatgctc ttgtgagaga gggtaaatat    2160
gctaatatcc ctgttattat tggagatcag aacgacgaag gtactttctt cggaacatcc    2220
tcactcaatg tgactaccga cgctcaggca agagagtact ttaagcaatc tttcgttcat    2280
gcttcagatg cagaaattga cactcttatg actgcttatc caggtgatat tactcaaggc    2340
```

```
tccccttttg acacaggcat tcttaacgct ctcactccac aattcaagag gatttcagca    2400
gttcttggcg atcttggttt taccctcgct agacgttatt tccttaatca ttacactggt    2460
ggaacaaagt attctttcct ttcaaaacag ctttccggtc tcccagtgct tggaactttc    2520
cactcaaacg acatcgtttt ccaggattat cttctcggtt ccggttctct tatttataat    2580
aacgctttca ttgcattcgc taccgacctt gatccaaata ctgctggact ccttgttaag    2640
tggcctgaat acacatcctc ttcccaaagt ggtaacaacc ttatgatgat caatgctctc    2700
ggtctttata ctggtaaaga caacttcaga accgcaggat acgatgctct tttctctaat    2760
cctccatcat tcttcgtgtg agagctcaac caataaataa taataataat aatgaataag    2820
aaaacaaagg ctttagcttg ccttttgttc actgtaaaat aataatgtaa gtactctcta    2880
taatgagtca cgaaacttt gcgggaataa aaggagaaat tccaatgagt tttctgtcaa    2940
atcttctttt gtctctctct ctctctcttt ttttttcctt tcttctgagc ttcttgcaaa    3000
acaaaaggca aacaataacg attggtccaa tgatagttag cttgatcgat gatatcttta    3060
ggaagtgttg gcaggacagg acatgatgta gaagactaaa attgaaagta ttgcagaccc    3120
aatagttgaa gattaacttt aagaatgaag acgtcttatc aggttcttca tgacttg      3177
```

<210> SEQ ID NO 52
<211> LENGTH: 20
<212> TYPE: DNA
<213> ORGANISM: Artificial Sequence
<220> FEATURE:
<223> OTHER INFORMATION: Synthetic primer

<400> SEQUENCE: 52
ctggtgcaaa ccttccagtt                                                20

<210> SEQ ID NO 53
<211> LENGTH: 20
<212> TYPE: DNA
<213> ORGANISM: Artificial Sequence
<220> FEATURE:
<223> OTHER INFORMATION: Synthetic primer

<400> SEQUENCE: 53
ttatcggatg cagaaccaca                                                20

<210> SEQ ID NO 54
<211> LENGTH: 5
<212> TYPE: PRT
<213> ORGANISM: Artificial Sequence
<220> FEATURE:
<223> OTHER INFORMATION: chemically synthesized fused protein

<400> SEQUENCE: 54

Ser Ala Pro Thr Ala
1               5

GLYCININ SIGNAL SEQUENCE FOR PRODUCING SECRETED PROTEINS IN PLANTS

BACKGROUND OF THE INVENTION

1. Field of the Invention

The present invention relates to methods for producing proteins secreted out of plant cells.

2. Description of the Related Art

When a heterologous protein gene is introduced into a plant host cell and is highly expressed, secreting the expressed heterologous protein into the extracellular apoplast to accumulate therein may be envisioned as a measure to reduce a load on the host cell.

Methods for secreting a heterologous protein into an extracellular apoplast may include a method of expressing the heterologous protein in the form of a fusion protein in which a signal sequence that directs endoplasmic reticulum (ER) transport is linked to the amino terminus of the heterologous protein. The signal sequence allows the linked protein to penetrate into the endoplasmic reticulum lumen, and the signal sequence is cleaved from the heterologous protein by a signal peptidase in the ER membrane to release the heterologous protein into the ER lumen. The heterologous protein is folded in the ER lumen, and then secreted into the extracellular apoplast by the intracellular transport system.

Glycinin is a soybean seed storage protein, and after it is translated in the form of a proglycinin precursor having a signal sequence for ER transport, the signal sequence is cleaved from the precursor in the ER membrane to release a proglycinin. Proglycinin forms a trimer in the EA and is transported into a protein storage vacuole, and then is processed into a mature glycinin to form a hexamer. Maruyama et al. (The Plant Cell, 2006, vol. 18, p. 1253-1273) reported that in an experiment of transiently expressing a green fluorescent protein (hereinafter, sometimes referred to as GFP) in a soybean immature seed, only when a glycinin signal sequence for ER transport that was flanked on its carboxy terminus by 9-amino acids sequence derived from a proglycinin amino-terminal region was fused to the amino terminus of a GFP to express, the GFP was secreted into the extracellular apoplast. Kawagoe et al. (The Plant Cell, 2005, vol. 17, p. 1141-1153) reported that in an experiment of expressing a GFP in a recombinant rice immature seed, when a glycinin signal sequence for ER transport that was flanked on its carboxy terminus by 2-amino acids sequence derived from a proglycinin amino-terminal region and a few other amino acids was fused to the amino terminus of a GFP to express, the GFP was not secreted into the extracellular apoplast.

In production of useful proteins, to maintain original useful properties such as enzyme activities or physiological functions of an intended heterologous protein, it is preferred that heterologous proteins to be produced have no additional heterologous sequences or short ones, if any.

SUMMARY OF THE INVENTION

It is an object of the present invention to provide improved methods for secreting an intended heterologous protein into an extracellular apoplast of a plant cell using a glycinin signal sequence for ER transport, in production of the heterologous protein in plant cells.

The present invention provides:

1. a method for producing a heterologous protein secreted out of a plant cell comprising:

introducing into a plant cell genome a DNA encoding an amino acid sequence that comprises a glycinin signal sequence for endoplasmic reticulum transport and an amino acid sequence of a heterologous protein, wherein the signal sequence is directly fused to the amino acid sequence of the heterologous protein or one or two amino acids are inserted between the signal sequence and the amino acid sequence of the heterologous protein; and expressing the DNA;

2. the method according to the item 1, wherein one amino acid is inserted between the signal sequence and the amino acid sequence of the heterologous protein;

3. the method according to the item 2, wherein the one amino acid is selected from among serine, alanine and methionine;

4. the method according to any one of the items 1 to 3, wherein the glycinin signal sequence for endoplasmic reticulum transport is the amino acid sequence of SEQ ID NO:1;

5. a method for producing a recombinant plant cell secreting a heterologous protein comprising:

introducing into a plant cell genome a DNA encoding an amino acid sequence that comprises a glycinin signal sequence for endoplasmic reticulum transport and an amino acid sequence of a heterologous protein, wherein the signal sequence is directly fused to the amino acid sequence of the heterologous protein or one or two amino acids are inserted between the signal sequence and the amino acid sequence of the heterologous protein;

6. a plant expression plasmid comprising a DNA encoding an amino acid sequence that comprises a glycinin signal sequence for endoplasmic reticulum transport and an amino acid sequence of a heterologous protein, wherein the signal sequence is directly fused to the amino acid sequence of the heterologous protein or one or two amino acids are inserted between the signal sequence and the amino acid sequence of the heterologous protein;

7. the plasmid according to the item 6, wherein one amino acid is inserted between the signal sequence and the amino acid sequence of the heterologous protein;

8. a DNA encoding an amino acid sequence that comprises a glycinin signal sequence for endoplasmic reticulum transport and an amino acid sequence of a heterologous protein, wherein one or two amino acids are inserted between the signal sequence and the amino acid sequence of the heterologous protein;

9. a plant cell with a genome into which a DNA encoding an amino acid sequence is introduced, the amino acid sequence comprising a glycinin signal sequence for endoplasmic reticulum transport and an amino acid sequence of a heterologous protein, wherein the signal sequence is directly fused to the amino acid sequence of the heterologous protein or one or two amino acids are inserted between the signal sequence and the amino acid sequence of the heterologous protein; and 10. a plant with a genome into which a DNA encoding an amino acid sequence is introduced, the amino acid sequence comprising a glycinin signal sequence for endoplasmic reticulum transport and an amino acid sequence of a heterologous protein, wherein the signal sequence is directly fused to the amino acid sequence of the heterologous protein or one or two amino acids are inserted between the signal sequence and the amino acid sequence of the heterologous protein, or a seed of the plant; and the like.

According to the present invention, it is possible to secrete an intended heterologous protein in a functional form into an extracellular apoplast of a plant cell without fusing a relatively long peptide to the heterologous protein, in production of the heterologous protein in plant cells.

DETAILED DESCRIPTION OF THE PREFERRED EMBODIMENTS

Figure 1:
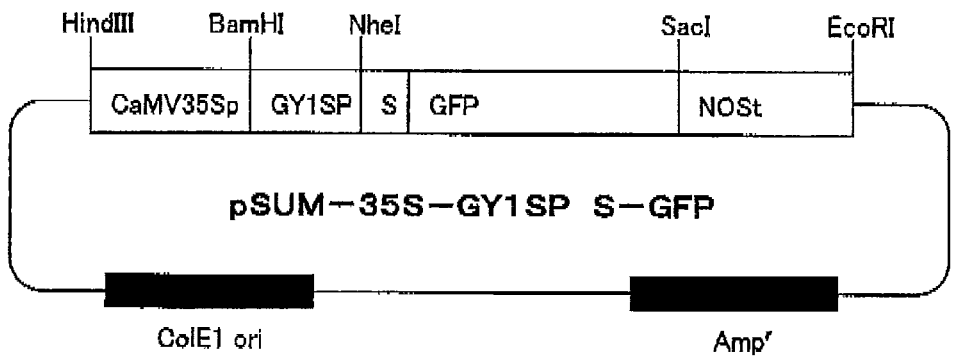
FIG. 1 is a structural schematic diagram of the plasmid pSUM-35S-GY1SP S-GFP.

In the present invention, the term "out of plant cells" means the outside of the plant cell membrane.

The term "extracellular apoplast" means a region outside of plant cell membrane, specifically includes a vessel or xylem, a cell wall, an intercellular space, and the like, and includes culture medium used in cell culture.

The term "secretion" in the present invention refers to transporting proteins into the extracellular apoplast.

In general, as the extracellular apoplast is low in protein content, mainly consists of water and ions, it may accumulate heterologous proteins in high concentration.

In the present specification, "an amino acid sequence that comprises a glycinin signal sequence for endoplasmic reticulum transport and an amino acid sequence of a heterologous protein, wherein the signal sequence is directly fused to the amino acid sequence of the heterologous protein or one or two amino acids are inserted between the signal sequence and the amino acid sequence of the heterologous protein" may be referred to as "an amino acid sequence used in the present invention".

The DNA encoding "an amino acid used in the present invention" may be referred to as a "DNA used in the present invention".

The "DNA used in the present invention" may be single-stranded DNA or double-stranded DNA.

"An amino acid sequence used in the present invention" is an amino acid sequence of a fusion protein containing an amino acid represented by the following (1) or (2).

In the present specification, an amino acid sequence is listed from the amino terminal to the carboxyl terminal.

(1) an amino acid sequence in which a glycinin signal sequence for endoplasmic reticulum transport is directly fused to an amino acid sequence of a heterologous protein.

(2) an amino acid sequence in which one or two amino acids are inserted between a glycinin signal sequence for endoplasmic reticulum transport and an amino acid sequence of a heterologous protein.

A glycinin signal sequence for endoplasmic reticulum transport used in the present invention is a signal sequence for transport into the endoplasmic reticulum (ER) located in the amino terminal of a proglycinin precursor. The signal sequence has a function to allow the protein linked to its carboxyl terminus to penetrate into the endoplasmic reticulum lumen and is cleaved off by a signal peptidase in the ER membrane. Five (5) subunits (G1 to G5) are present in glycinin, and a signal sequence for ER transport of each subunit is known (Nielsen et al., The Plant Cell (1989) Vol. 1, pp 313-328) (SEQ ID NOs: 1 to 5). A glycinin signal sequence for endoplasmic reticulum transport used in the present invention may specifically include the amino acid sequence of any one of SEQ ID NOs: 1 to 5, and preferably the amino acid sequence of SEQ ID NO: 1, but it is not limited to as far as it has a function as a glycinin signal sequence for endoplasmic reticulum transport. For example, glycinin signal sequence for endoplasmic reticulum transport to be found in the future and variant of glycinin signal sequence for endoplasmic reticulum transport may be used.

Signal sequence for ER transport of subunit G1:

MAKLVFSLCFLLFSGCCFA      (SEQ ID NO: 1)

Signal sequence for ER transport of subunit G2

MAKLVLSLCFLLFSGCFA       (SEQ ID NO: 2)

Signal sequence for ER transport of subunit G3:

MAKLVLSLCFLLFSGCCFA      (SEQ ID NO: 3)

Signal sequence for ER transport of subunit G4:

MGKPFTLSLSSLCLLLLSSACFA   (SEQ ID NO: 4)

Signal sequence for ER transport of subunit G5:

MGKPFFTLSLSSLCLLLLSSACFA  (SEQ ID NO: 5)

A "heterologous protein" in the present invention is a protein intended to be produced by introducing its structural gene into a host plant cell genome, and a protein that is not native to the amino acid sequence linked to its amino terminus. The "heterologous protein" includes not only a protein which is not produced naturally in the host plant cell, but also a protein naturally produced in the host plant cell. When the "heterologous protein" is directly linked to a glycinin signal sequence for endoplasmic reticulum transport, it is a protein other than glycinin.

A "heterologous protein" in the present invention is preferably a mature protein. A "heterologous protein" in the present invention is preferably a protein suitable to be expressed in a plant cell. The present invention is suitable for producing proteins which are not operably folded when expressed in a prokaryotic cell such as *E. coli* and which are operably folded when expressed in plant cells. A "heterologous protein" may include industrially useful proteins such as industrial enzymes, vaccines, physiologically active materials, and antibodies. Specifically, a "heterologous protein" may include lipase (for example, refer to Longhi et al., 1992, Biochimica et Biophysics Acta (1992) Vol. 1131 (2), pp 227-232), amylase, pectinase, β-glucanase, phytase, lactase, and the like as an industrial enzyme; chicken Newcastle disease vaccine, vaccine against porcine edema disease, vaccine against porcine protozoal disease, hepatitis B vaccine, and the like as a vaccine; hematopoietic factor, hormone, interferons, and the like as a physiologically active material; and immunoglobulin and the like as an antibody.

A "heterologous protein" in the present invention is preferably a protein which does not have a sequence to reduce the extracellular secretion efficiency. Examples of the sequence to reduce the extracellular secretion efficiency may include an endoplasmic reticulum retention signal sequence and the amino acid sequence of any one of SEQ ID NOs: 1 to 3 described in U.S. Pat. No. 7,369,628.

A "heterologous protein" in the present invention is preferably a protein other than soybean glycinin.

Amino acid sequences of these proteins may be obtained by using protein engineering techniques and genetic engineering techniques known in the art, or may be obtained from a variety of databases available in the art. Nucleotide sequences encoding amino acid sequences of these proteins may be obtained by using conventional genetic engineering techniques, or may be obtained from a variety of databases available in the art.

In the present invention, a glycinin signal sequence for endoplasmic reticulum transport is directly linked to an amino acid sequence of a heterologous protein or one or two amino acids are inserted between the signal sequence and an amino acid sequence of a heterologous protein. Depending on the property of a desired heterologous protein, but it may be preferable that one or two amino acids are inserted between the signal sequence and the amino acid sequence of the heterologous protein for a good yield of the heterologous protein to be obtained without degradation, and may be more preferable that one amino acid is inserted between the signal sequence and the amino acid sequence of the heterologous protein. The "one amino acid" may include one amino acid selected among serine, alanine, and methionine. The sequence of the "two amino acids" is preferably an amino acid sequence other than FS (phenylalanine-serine).

A DNA encoding "an amino acid sequence that comprises a glycinin signal sequence for endoplasmic reticulum transport and an amino acid sequence of a heterologous protein, wherein the signal sequence is directly fused to the amino acid sequence of the heterologous protein or one or two amino acids are inserted between the signal sequence and the amino acid sequence of the heterologous protein" may be prepared by conventional genetic engineering techniques. For example, based on nucleotide sequences, "a DNA used in the present invention" is chemically synthesized. A DNA encoding a heterologous protein may be linked in frame to a DNA comprising (a) a nucleotide sequence encoding a glycinin signal sequence for endoplasmic reticulum transport or (b) a nucleotide sequence in which a nucleotide sequence encoding one or two amino acids is added to the 3' end of the nucleotide sequence of (a) by using conventional genetic engineering techniques. More specifically, it may be prepared based on the methods described in Examples below.

In the production method of the present invention, the "DNA used in the present invention" described above is introduced into a plant cell genome to be expressed.

A method of introducing DNA may include genetic engineering methods known in the art. For example, a plant expression plasmid containing "a DNA used in the present invention" is introduced by using a genetic Cell engineering technique suitable for a host plant cell. These techniques may include an *Agrobacterium* method, particle gun method, electroporation method, and calcium phosphate method.

In response to a gene transfer method employed, a plant expression plasmid containing "a DNA used in the present invention" may be constructed by inserting the "DNA used in the present invention" into, for example, a Ti plasmid-derived vector such as pBI101 and pBI121, or a Ri plasmid-derived vector, or a conventional pUC-based *E. coli* vector such as pBI221 using conventional genetic engineering methods.

The plant expression plasmid contains a promoter and a terminator to express a fusion protein of the present invention.

The corresponding promoter is not specifically limited to as far as it can function in a plant cell, and include a constitutive promoter such as cauliflower mosaic virus 35S promoter (International Patent Publication WO84/02913), ubiquitin promoter (International Patent Publication WO01/094394) and actin promoter (International Patent Publication WO00/070067), a tissue-specific promoter such as soybean seed glycinin promoter (European Patent Publication EP0571741), carrot CR16G1 promoter (U.S. Pat. No. 5,959, 176) and common bean phaseolin promoter (International Patent Publication WO91/013993), and a chemical inducible promoter such as corticosteroid responsive promoter (Aoyama T & Chua N H, 1997, Plant J. 11, 605-612; U.S. Pat. No. 6,063,985) and ethanol responsive promoter (Caddick M X et al., 1998, Nature Biotech, 16, 177-180; International Patent Publication WO93/21334).

The terminator is not specifically limited to as far as it can function in a plant cell, and may include, NOS terminator (International Patent Publication WO84/02913), soybean seed glycinin terminator (European Patent Publication EP0571741) and carrot CR16 terminator (U.S. Pat. No. 7,202,083).

Also, the plant expression plasmid may contain a selective marker such as auxotrophic marker or drug resistant marker.

A cell with a genome into which "a DNA used in the present invention" has been introduced may be selected and purified by characteristics of the selective marker, for example, resistance to kanamycin, introduced along with the DNA.

Since the plant expression plasmid has been incorporated into the genome of a plant cell, a sequence of "a DNA used in the present invention" is transferred to the genome of a daughter cell after cell division and as a result, it is possible to stably express the DNA even in the progeny.

A plant cell with a genome into which "a DNA used in the present invention" will be introduced, that is, a host plant cell is preferably a cell of a plant for which gene transfer method, tissue culture method, technique of redifferentiation from a cell or a callus, and the cultivation technique are established. Also, the host plant cell is preferably a cell of a plant species important for industry such as agriculture or useful in studies such as genome analyses. These plants may include, soybean, common bean, green pea, peanut, castor bean, rice, corn, cotton, rapeseed, wheat, barley, cucumber, eggplant, carrot, potato, taro, sweet potato, pumpkin, garlic, onion, Japanese cedar, pine, willow, poplar, eucalyptus, tobacco, birdsfoot trefoil, alfalfa, clover, thale cress, sorghum, sesame, sunflower, Jerusalem artichoke, switchgrass, pampas grass, Jatropha curcas, oil palm, coconut palm, olive, sugarcane, sugar beet, cassaya, and kenaf.

A cell with a genome into which "a DNA used in the present invention" has been introduced may be cultured under suitable conditions by using MS culture medium and the like.

From the cell into which "a DNA used in the present invention" has been introduced, a plant (body) into which "a DNA used in the present invention" has been introduced may be obtained by the conventional redifferentiation methods. Also, from the plant, its seed may be obtained.

A heterologous protein of interest may be produced by expressing and secreting by a plant cell of the present invention, or a plant of the present invention.

The resulting produced protein can be recovered appropriately by a combination of ordinary isolation and purification methods. For example, culture of the plant cell of the present invention or homogenized fraction of the plant or plant cell of the present invention can be recovered and used as a fraction containing the "heterologous protein" of interest. A fraction containing the "heterologous protein" of interest can also be obtained by a centrifugation of the culture after completion of the culture and subsequent recovering of the supernatant. A further purified "heterologous protein" of interest can be recovered by subjecting the supernatant fraction described above to various chromatographic procedures such as ion exchange chromatography, hydrophobic interaction chromatography, gel filtration chromatography, affinity chromatography and the like.

A method of recovering an extracellular apoplast solution in which "heterologous proteins" are accumulated may include methods described in experimental protocols (for example, 'Experimental protocol for proteins of a plant. The functions and structures of proteins approached from genes and organisms', Kenzo Nakamura at al., 1998, SHUJUN Co., Ltd., ISBN 4-87962-180-3) or literatures (for example, Boernke at al., Planta (2002) Vol. 214, pp 356-364). For example, a buffer having a high ionic strength such as 1 M sodium chloride or 1 M potassium chloride may be sucked into a plant cell under low pressures and then the cell may be centrifuged at low speeds to recover an extracellular apoplast solution.

EXAMPLES

The present invention will be described in detail with reference to examples, but the present invention is not limited to the examples.

Example 1

Construction of a Green Fluorescent Protein Expression Plasmid

In order to express Aequorea Victoria-derived green fluorescent protein (hereinafter, it may be referred to as GFP) in a plant cell, an expression plasmid was constructed, the plasmid containing a DNA in which a DNA encoding a glycinin signal sequence for endoplasmic reticulum transport (hereinafter, it may referred to as GY1SP) and a DNA encoding a green fluorescent protein has been linked without causing a codon frame shift (that is, in-frame).

(1) Construction of a GFP Secretory Expression Plasmid

An oligonucleotide consisting of the nucleotide sequence of SEQ ID NO: 6 and encoding a green fluorescent protein was synthesized. A PCR was performed by using the synthesized oligonucleotide as a template, and an oligonucleotide consisting of the nucleotide sequence of SEQ ID NO: 7 and an oligonucleotide consisting of the nucleotide sequence of SEQ ID NO; 8 as primers to amplify a DNA fragment encoding GFP and having a NheI site and a SacI site respectively at each of the 5'- and 3'-end of the fragment. For the PCR, a DNA polymerase (trade name: KOD-Plus, manufactured by TOYOBO Co., Ltd.) was used and conditions of the reactions were as followed: incubation at 94° C. for 2 minutes, followed by 30 cycles each for 94° C. for 30 seconds, 50° C. for 30 seconds, and 68° C. for 60 seconds; and followed by incubation at 68° C. for 3 minutes. The amplified DNA fragment was purified from the reaction Solution by using a DNA fragment purification kit (trade name: MagExtractor-PCR & Gel Clean Up, manufactured by TOYOBO Co., Ltd.), and the purified DNA fragment was ligated by using a gene cloning kit (trade name: TaKaRa BKL Kit, manufactured by TaKaRa Co., Ltd.) to the SmaI site of the plasmid pUC118. The ligation product was introduced into competent cells of *E. coli* DH5α strains (manufactured by TOYOBO Co., Ltd.) and ampicillin resistant strains were selected. Nucleotide sequences of plasmids from the selected resistant strains were analyzed by using a reaction kit for nucleotide sequence analysis (trade name: BigDye Terminator v3.1 Cycle Sequencing Kit, manufactured by Applied Biosystems Japan. Ltd ABI) and a nucleotide sequence analyzer (trade name: ABI Prism 3100 Genetic Analyzer, manufactured by Applied Biosystems Japan. Ltd ABI). A plasmid having an intended nucleotide sequence was digested with NheI and SacI and was obtained a 0.7 kbp DNA fragment encoding a polypeptide in which a serine residue has been fused to the amino terminus of GFP.

```
SEQ ID NO: 6: 5'-

ATGGTGAGCAAGGGCGAGGAGCTGTTCACCGGGGTGGTGCCCATCCTGGTCGAGCTGGACGG

CGACGTGAACGGCCACAAGTTCAGCGTGTCCGGCGAGGGCGAGGGCGATGCCACCTACGGCA

AGCTGACCCTGAAGTTCATCTGCACCACCGGCAAGCTGCCCGTGCCCTGGCCCACCCTCGTG

ACCACCTTCACCTACGGCGTGCAGTGCTTCAGCCGCTACCCCGACCACATGAAGCACCACGA

CTTCTTCAAGTCCGCCATGCCCGAAGGCTACGTCCAGGAGCGCACCATCTTCTTCAAGGACG

ACGGCAACTACAAGACCCGCGCCGAGGTGAAGTTCGAGGGCGACACCCTGGTGAACCGCATC

GAGCTGAAGGGCATCGACTTCAAGGAGGACGGCAACATCCTGGGGCACAAGCTGGAGTACAA

CTACAACAGCCACAACGTCTATATCATGGCCGACAAGCAGAAGAACGGCATCAAGGTGAACT

TCAAGATCCGCCACAACATCGAGGACGGCAGCGTGCAGCTCGCCGACCACTACCAGCAGAAC

ACCCCCATCGGCGACGGCCCCGTGCTGCTGCCCGACAACCACTACCTGAGCACCCAGTCCGC

CCTGAGCAAAGACCCCAACGAGAAGCGCGATCACATGGTCCTGCTGGAGTTCGTGACCGCCG
```

-continued

CCGGGATCACTCACGGCATGGACGAGCTGTACAAGTAA-3'

SEQ ID NO: 7: 5'-gctagcgtgagcaagggcgaggagctgttcacc-3'

SEQ ID NO: 8: 5'-gagctcttacttgtacagctcgtccatgccgtg-3'

Terminally-phosphorylated synthetic oligonucleotides with the nucleotide sequences of SEQ ID NOs:9 and 10 respectively were mixed at an equivalent mole ratio, heated at 65° C. for 5 minutes, and then cooled slowly to room temperature to prepare a linker encoding a glycinin signal sequence for ER transport (SEQ ID NO: 1). The prepared linker and the 0.7 kbp DNA fragment encoding the polypeptide in which a serine residue has been fused to the amino terminus of GFP were ligated to the plasmid pBI221 (GenBank Accession Number AF502128) digested with BamHI and SacI and transformed into *E. coli* in a similar manner. Nucleotide sequences of selected resistant strains were analyzed and was obtained the plasmid pSUM-35S-GY1SP S-GFP (FIG. 1) containing the nucleotide sequence of SEQ ID NO: 11 and expressing a fusion protein in which a serine residue has been inserted between GY1SP and GFP.

round PCR, a DNA polymerase (trade name: PrimeSTAR HS DNA Polymerase, manufactured by TaKaRa Co., Ltd.) was used and conditions of the reactions were 30 cycles each for 98° C. for 10 seconds, 55° C. for 5 seconds, and 72° C. for 30 seconds. The second-round PCRs were performed in the same manner as the first-round PCR except that the incubation time at 72° C. was modified to 60 seconds.

Each of the amplified DNA fragments was purified, digested with BamHI and SacI, and inserted between the BamHI site and the SacI site of the plasmid pSUM-355-GY1SP S-GFP by replacing the DNA fragment of pSUM-355-GY1SP S-GFP encoding a fusion protein in which a serine residue has been inserted between GY1SP and GFP with the BamHI and SacI-digested amplified DNA fragment to obtain the following plasmids.

SEQ ID NO: 9: 5'-gatccatggccaagctagttttttccctttgttttctgcttttcagtggctgctgcttcg-3'

SEQ ID NO: 10: 5'-ctagcgaagcagcagccactgaaaagcagaaaacaaagggaaaaaactagcttggccatg-3'

SEQ ID NO: 11: 5'-
GGATCCATGGCCAAGCTAGTTTTTTCCCTTTGTTTTCTGCTTTTCAGTGGCTGCTGCTTCGC

TAGCGTGAGCAAGGGCGAGGAGCTGTTCACCGGGGTGGTGCCCATCCTGGTCGAGCTGGACG

GCGACGTGAACGGCCACAAGTTCAGCGTGTCCGGCGAGGGCGAGGGCGATGCCACCTACGGC

AAGCTGACCCTGAAGTTCATCTGCACCACCGGCAAGCTGCCCGTGCCCTGGCCCACCCTCGT

GACCACCTTCACCTACGGCGTGCAGTGCTTCAGCCGCTACCCCGACCACATGAAGCAGCACG

ACTTCTTCAAGTCCGCCATGCCCGAAGGCTACGTCCAGGAGCGCACCATCTTCTTCAAGGAC

GACGGCAACTACAAGACCCGCGCCGAGGTGAAGTTCGAGGGCGACACCCTGGTGAACCGCAT

CGAGCTGAAGGGCATCGACTTCAAGGAGGACGGCAACATCCTGGGGCACAAGCTGGAGTACA

ACTACAACAGCCACAACGTCTATATCATGGCCGACAAGCAGAAGAACGGCATCAAGGTGAAC

TTCAAGATCCGCCACAACATCGAGGACGGCAGCGTGCAGCTCGCCGACCACTACCAGCAGAA

CACCCCCATCGGCGACGGCCCCGTGCTGCTGCCCGACAACCACTACCTGAGCACCCACTCCG

CCCTGAGCAAAGACCCCAACGAGAAGCGCGATCACATGGTCCTGCTGGAGTTCGTGACCGCC

GCCGGGATCACTCACGGCATGGACGAGCTGTACAAGTAAGAGCTC-3'

Figure 2:
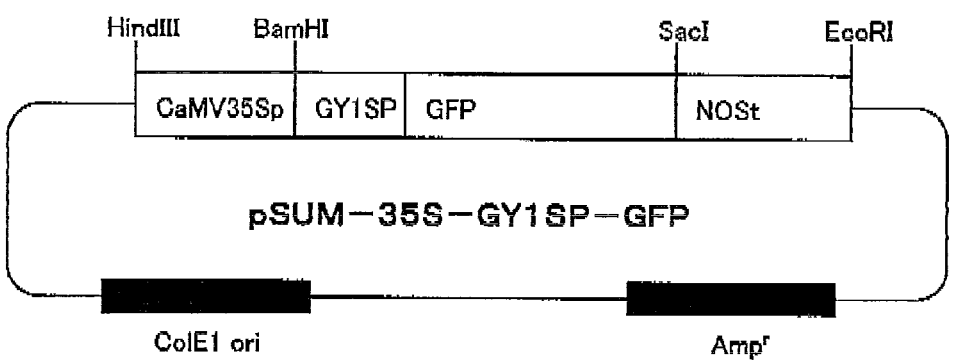
FIG. 2 is a structural schematic diagram of the plasmid pSUM-35 S-GY1SP-GFP.

A first-round PCR was performed by using the plasmid pSUM-35S-GY1SP S-GFP as a template, an oligonucleotide consisting of the nucleotide sequence of SEQ ID NO: 12 as a forward primer, and an oligonucleotide consisting of the nucleotide sequence of SEQ ID NO: 13, 14, or 15 as a reverse primer for modification, respectively. Second-round PCRs were performed by using a portion of each reaction solution of the first-round PCR as a template, the oligonucleotide consisting of the nucleotide sequence of SEQ ID NO: 12 as a forward primer, and an oligonucleotide consisting of the nucleotide sequence of SEQ ID NO: 16 as a reverse primer, to amplify a DNA fragment having a BamHI site and a SacI site respectively at each of the 5'- and 3'-end of the fragment and encoding a fusion protein in which an alternative amino acid residue is inserted between GY1SP and GFP. For the first- By using the oligonucleotide consisting of the nucleotide sequence of SEQ ID NO: 13 as a reverse primer for modification in the first-round PCR, was obtained a plasmid pSUM-35S-GY1SP-GFP (FIG. 2) expressing a fusion protein in which GY1SP and GFP are directly linked with no additional amino acid residue insertion.

Figure 3:
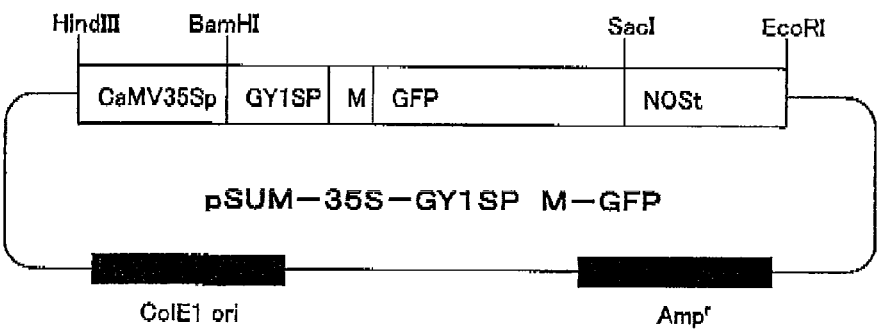
FIG. 3 is a structural schematic diagram of the plasmid pSUM-35S-GY1SP M-GFP.

By using the oligonucleotide consisting of the nucleotide sequence of SEQ ID NO: 14 as a reverse primer for modification in the first-round PCR, was obtained a plasmid pSUM-35S-GY1SP M-GFP (FIG. 3) expressing a fusion protein in which a methionine residue has been inserted between GY1SP and GFP.

Figure 4:
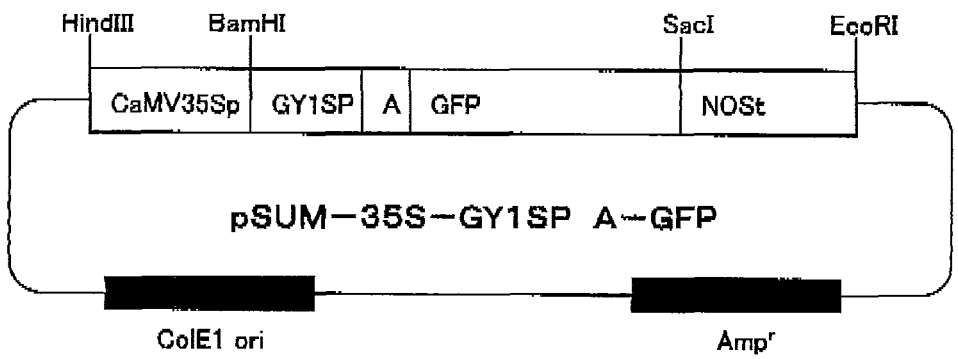
FIG. 4 is a structural schematic diagram of the plasmid pSUM-35S-GY1SP A-GFP.

By using the oligonucleotide consisting of the nucleotide sequence of SEQ ID NO: 15 as a reverse primer for modification in the first-round PCR, was obtained a plasmid pSUM- 35S-GY1SP A-GFP (FIG. 4) expressing a fusion protein in which an alanine residue has been inserted between GY1SP and GFP.

```
SEQ ID NO: 12: 5'-gagtcaggatccatggccaagctagttttttc
c-3'
SEQ ID NO: 13: 5'-cttgctcacagcgaagcagcagcc-3'
SEQ ID NO: 14: 5'-cttgctcaccatagcgaagcagcagcc-3'
SEQ ID NO: 15: 5'-cttgctcacagcagcgaagcagca-3'
SEQ ID NO: 16: 5'-gttcgagagctcttacttgtacagctcgtcca
t-3'
```

By using an oligonucleotide consisting of the nucleotide sequence of SEQ ID NO: 17 as a reverse primer for modification in the first-round PCR, is obtained a plasmid expressing a fusion protein in which a glycine residue has been inserted between GY1SP and GFP.

By using an oligonucleotide consisting of the nucleotide sequence of SEQ ID NO: 18 as a reverse primer for modification in the first-round PCR, is obtained a plasmid expressing a fusion protein in which a leucine residue has been inserted between GY1SP and GFP.

By using an oligonucleotide consisting of the nucleotide sequence of SEQ ID NO: 19 as a reverse primer for modification in the first-round PCR, is obtained a plasmid expressing a fusion protein in which an isoleucine residue has been inserted between GY1SP and GFP.

By using an oligonucleotide consisting of the nucleotide sequence of SEQ ID NO: 20 as a reverse primer for modification in the first-round PCR, is obtained a plasmid expressing a fusion protein in which a valine residue has been inserted between GY1SP and GFP.

By using an oligonucleotide consisting of the nucleotide sequence of SEQ ID NO: 21 as a reverse primer for modification in the first-round PCR, is obtained a plasmid expressing a fusion protein in which a proline residue has been inserted between GY1SP and GFP.

By using an oligonucleotide consisting of the nucleotide sequence of SEQ ID NO: 22 as a reverse primer for modification in the first-round PCR, is obtained a plasmid expressing a fusion protein in which a threonine residue has been inserted between GY1SP and GFP.

By using an oligonucleotide consisting of the nucleotide sequence of SEQ ID NO: 23 as a reverse primer for modification in the first-round PCR, is obtained a plasmid expressing a fusion protein in which a histidine residue has been inserted between GY1SP and GFP.

By using an oligonucleotide consisting of the nucleotide sequence of SEQ ID NO: 24 as a reverse primer for modification in the first-round PCR, is obtained a plasmid expressing a fusion protein in which a glutamine residue has been inserted between GY1SP and GFP.

By using an oligonucleotide consisting of the nucleotide sequence of SEQ ID NO: 25 as a reverse primer for modification in the first-round PCR, is obtained a plasmid expressing a fusion protein in which a glutamic acid residue has been inserted between GY1SP and GFP.

By using an oligonucleotide consisting of the nucleotide sequence of SEQ ID NO 26 as a reverse primer for modification in the first-round PCR, is obtained a plasmid expressing a fusion protein in which an asparagine residue has been inserted between GY1SP and GFP.

By using an oligonucleotide consisting of the nucleotide sequence of SEQ ID NO: 27 as a reverse primer for modification in the first-round PCR, is obtained a plasmid expressing a fusion protein in which an aspartic acid residue has been inserted between GY1SP and GFP.

By using an oligonucleotide consisting of the nucleotide sequence of SEQ ID NO: 28 as a reverse primer for modification in the first-round PCR, is obtained a plasmid expressing a fusion protein in which a lysin residue has been inserted between GY1SP and GFP.

By using an oligonucleotide consisting of the nucleotide sequence of SEQ ID NO 29 as a reverse primer for modification in the first-round PCR, is obtained a plasmid expressing a fusion protein in which a cysteine residue has been inserted between GY1SP and GFP.

By using an oligonucleotide consisting of the nucleotide sequence of SEQ ID NO: 30 as a reverse primer for modification in the first-round PCE, is obtained a plasmid expressing a fusion protein in which an arginine residue has been inserted between GY1SP and GFP.

By using an oligonucleotide consisting of the nucleotide sequence of SEQ ID NO: 31 as a reverse primer for modification in the first-round PCR, is obtained a plasmid expressing a fusion protein in which a tyrosine residue has been inserted between GY1SP and GFP.

By using an oligonucleotide consisting of the nucleotide sequence of SEQ ID NO: 32 as a reverse primer for modification in the first-round PCR, is obtained a plasmid expressing a fusion protein in which a tryptophan residue has been inserted between GY1SP and GFP.

By using an oligonucleotide consisting of the nucleotide sequence of SEQ ID NO: 33 as a reverse primer for modification in the first-round PCR, 18 obtained a plasmid expressing a fusion protein in which a phenylalanine residue has been inserted between GY1SP and GFP.

By using an oligonucleotide consisting of the nucleotide sequence of SEQ ID NO: 34 as a reverse primer for modification in the first-round PCR, is obtained a plasmid expressing a fusion protein in which a serine residue and a glycine residue have been inserted between GY1SP and GET.

By using an oligonucleotide consisting of the nucleotide sequence of SEQ ID NO: 35 as a reverse primer for modification in the first-round PCR, is obtained a plasmid expressing a fusion protein in which a serine residue and an alanine residue have been inserted between GY1SP and GFP.

By using an oligonucleotide consisting of the nucleotide sequence of SEQ ID NO: 36 as a reverse primer for modification in the first-round PCR, is obtained a plasmid expressing a fusion protein in which an alanine residue and a glycine residue have been inserted between GY1SP and GFP.

```
SEQ ID NO: 17: 5'-cttgctcacgccagcgaagcagca-3'
SEQ ID NO: 18: 5'-cttgctcacaagagcgaagcagcagcc-3'
SEQ ID NO: 19: 5'-cttgctcacgatagcgaagcagcagcc-3'
SEQ ID NO: 20: 5'-cttgctcacaacagcgaagcagcagcc-3'
SEQ ID NO: 21: 5'-cttgctcacgggagcgaagcagca-3'
SEQ ID NO: 22: 5'-cttgctcacagtagcgaagcagcagcc-3'
SEQ ID NO: 23: 5'-cttgctcacgtgagcgaagcagca-3'
SEQ ID NO: 24: 5'-cttgctcacttgagcgaagcagcagcc-3'
SEQ ID NO: 25: 5'-cttgctcacttcagcgaagcagcagcc-3'
```

-continued

SEQ ID NO: 26: 5'-cttgctcacgttagcgaagcagcagcc-3'

SEQ ID NO: 27: 5'-cttgctcacatcagcgaagcagcagcc-3'

SEQ ID NO: 28: 5'-cttgctcaccttagcgaagcagcagcc-3'

SEQ ID NO: 29: 5'-cttgctcacgcaagcgaagcagca-3'

SEQ ID NO: 30: 5'-cttgctcactctagcgaagcagcagcc-3'

SEQ ID NO: 31: 5'-cttgctcacgtaagcgaagcagcagcc-3'

SEQ ID NO: 32: 5'-cttgctcacccaagcgaagcagca-3'

SEQ ID NO: 33: 5'-cttgctcacgaaagcgaagcagcagcc-3'

SEQ ID NO: 34: 5'-cttgctcacgccgctagcgaagca-3'

SEQ ID NO: 35: 5'-cttgctcacagcgctagcgaagcagca-3'

SEQ ID NO: 36: 5'-cttgctcacgccagcagcgaagca-3'

(2) Construction of a Get-Expressing Binary Vector for Infection Introduction

Each of the plasmids described in Example 1(1) is digested with HindIII and EcoRI to obtain a 1.9-kbp DNA fragment. Each of the obtained DNA fragments is ligated to the plasmid pBI121 (GenBank Accession Number AF485783) previously-digested with BamHI and SacI to obtain a binary vector plasmid expressing a fusion protein in which GY1SP and GFP are directly linked or one or two amino acids are inserted between GY1SP and GFP.

Example 2

Analysis of GFP Expression in Recombinant Tobacco Cultured Cells (1) Introduction of GFP Expression Plasmid into Tobacco Cultured Cells and Selection of Recombinant Cultured Cells An expression plasmid prepared in Example 1(1) was introduced into suspension cultured tobacco BY-2 cells by using a gene transfer system (trade name: PDS-1000/He System, manufactured by Bio-Rad Co., Ltd.). The preparation of cultured cells for gene transfer and gene transfer manipulation were conducted according to a method by IIDA at al. (Experimental Study Gene Transfer Experimental Method 1—Particle gun method—, Plant Cell Engineering, 1992, Vol. 4, No. 1, pp 43-48).

Three (3) to 5 days after the gene transfer manipulation, cultured cells were transferred onto a modified MS medium (MS inorganic salts (Murashige and Skoog, Physol. Plant. (1962) Vol. 15, pp 473-493), 3% sucrose, 1 μM 2,4-D, 1 mg/L thiamin-HCl, 100 mg/L myo-inositol, 200 mg/L $KH_2PO_4$) containing 30 mg/L of kanamycin and solidified with 0.8% agar and cultured in the dark at 23 to 25° C. for 1 month to select cell masses resistant to kanamycin. The selected cell masses were cultured on a modified MS agar medium containing 200 mg/L of kanamycin for another 3 weeks, grown cell masses were transferred to a fresh medium with the same composition, and then another culture for 3 to 4 weeks was further performed twice to establish recombinant cell strains. After 2 weeks of rotary culture of the obtained cell strains was performed in a modified MS liquid medium containing 200 mg/L of kanamycin in the dark at 23 to 25° C. at 140 rpm, another 2 weeks of culture was performed in a fresh medium under the same conditions to purify the recombinant cell strains and stabilize the growth of each cell strain.

Subsequently, a rotary culture of the recombinant cell strains was performed in a modified MS liquid medium without kanamycin under the same conditions, and 0.3 to 0.4 g of cells were transferred onto a fresh medium just before the cell growth would reach a saturated state to subcultures (2) Analysis of GFP Secretion Amount in Recombinant Tobacco Cultured Cells GFP secreted from the recombinant cultured cell obtained as described above into a culture medium and GFP accumulating in the cells were quantitatively measured by using a Western blotting method and an immunostaining method to calculate the secretion amount of the GFP.

When the growth rate was increasing exponentially as a result of a rotary culture of the recombinant cultured cells, 20 mL of the culture was recovered and centrifuged at 8,000 rpm for 10 minutes at room temperature and obtained a culture supernatant and cultured cells. The culture supernatant was concentrated by using a centrifugal filter unit (trade name: Centriprep YM-10, manufactured by Millipore Co. Ltd.) until the volume of the supernatant was reduced to about 1/200 of the original volume, and the concentrate obtained was used as a medium fraction. The cultured cells of 0.4 g were frozen with liquid nitrogen, glass beads (diameter 0.25 to 0.5 mm) of the same weight as the cell weight and 300 μL of PBS buffer were added, and then the cells were ground by a grinding apparatus (trade name: Mixermill MM-300, manufactured by QIAGEN Co., Ltd.). After the obtained ground product was centrifuged at 15,000 rpm, at 4° C. for 5 minutes, the supernatant was recovered and centrifuged at 15,000 rpm, at 4° C. for 5 minutes. The supernatant was recovered and used as a whole cell fraction. An aliquot of each fraction was collected and was subjected to a measurement of the protein concentration by using a protein coloration reagent (trade name: Bio-Rad Protein Assay Dye Reagent Concentrate, manufactured by Bio-Rad Co., Ltd.) and a bovine serum albumin preparation (manufacture by Sigma Co., Ltd.) as a standard.

The aliquot of each fraction and equal volume of the reagent buffer (2-fold concentrate, containing 2-mercapto ethanol, manufacture by Nacalai Teaque, Inc.) were mixed, and the mixture was subjected to a heat treatment at 100° C. for 3 minutes, and the resulting mixture was stored in ice. The mixture was applied to a SDS-PAGE gel (trade name: multi gel II Mini, manufactured by Cosmo Bio Co., Ltd.) and was electrophoresed under current of 30 mA per gel in the SDS-PAGE electrophoresis buffer (0.1% SDS, 25 mM tris, 192 mM glycine) for 1 hour. A recombinant GFP manufactured by Cosmo Bio Co., Ltd was electrophoresed as a standard for protein content determination. After the electrophoresis, the gel was slowly shook in a transfer buffer (0.0375% SOS, 48 mM tris, 39 mM glycine, 20% methanol) at room temperature for 15 minutes, and then was subjected to electroblotting by using a Trans blotting SD cell manufactured by Bio-Rad Co., Ltd. at 10 V for 1 hour to transfer proteins from the gel to a PVDF membrane (trade name: Immobilon-P, manufactured by Millipore Co., Ltd.). After the membrane was washed with a washing buffer (TBS buffer containing 0.1% Tween) for 10 minutes, the membrane was slowly shook in a washing buffer containing 2% of ECL Advance Blocking Agent (manufactured by GE HealthCare Co., Ltd.) for 1 hour at room temperature to perform a blocking. Subsequently, the membrane was washed twice with a washing buffer for 5 minutes, and then it was slowly shook in a 4,000-fold dilution of GFP Epitope Tag manufactured by Affinity BioReagents Co., Ltd. with Can Get Signal Immunoreaction Enhancer Solution manufactured by TOYOBO Co., Ltd. at room temperature for 40 minutes as a primary antibody reaction. After the membrane was washed with a washing buffer once for 2 minutes, twice for 5 minutes, and once for 15 minutes, the membrane was slowly shook in 5,000-fold dilutions of ECL Anti-rabbit IgG, Horseradish Peroxidase-Liked Species-Specific Whole Antibody from donkey, manufactured by GE HealthCare Co., Ltd. and S-Protein-HRP conjugate, manufactured by GE Healthcare, with Can Get Signal Immunoreaction Enhancer Solution, manufactured by TOYOBO CO., Ltd. at room temperature for 1 hour as a secondary antibody reaction. Subsequently, after the membrane was washed three times with a washing buffer for 5 minutes. The membrane was subjected to GFP signal detection by using ECL Advanced Western Blotting Detection Kit manufactured by GE Healthcare Co., Ltd., a chemiluminescence detection device (trade name: ChemiDoc XRS, manufactured by Bio-Rad Co., Ltd.) and an image analysis software (trade name: Quantity One, manufactured by Bio-Rad Co., Ltd.) and the signal intensity was measured.

In the medium fraction of the each recombinant tobacco cultured cells to which the plasmid pSUM-35S-GY1SP-GFP, pSUM-35S-GY1SP S-GFP, pSUM-35S-GY1SP M-GFP, or pSUM-355-GY1SP A-GFP has been introduced, a signal of GFP having an appropriate molecular weight was detected. Each of the secretion amounts of GFP per milliliter of culture was calculated as 2.4 ng for pSUM-35S-GY1SP-GFP introduced cells, 20.7 ng for pSUM-35S-GY1SP S-GFP introduced cells, 10.1 ng for pSUM-355-GY1SP M-GFP introduced cells, and 1.8 ng for pSUM-35S-GY1SP A-GFP introduced cells, and from these results, it was apparent that heterologous proteins were secreted out of the plant cells. Also, each of the ratios of GFP not degraded to GFP secreted was calculated as 17% for pSUM-35-GY1SP-GFP introduced Cells, 61% for pSUM-35S-GY1SP S-GFP introduced cells, 49% for pSUM-355-GY1SP M-GFP introduced cells, and 38% for pSUM-35S-GY1SP A-GFP introduced cells. From these results, it could be seen that an intended heterologous protein was extracellularly secreted when GY1SP is linked to the heterologous protein, and also it has a greater tendency to have high yields of the heterologous protein without any degradation when one amino acid is inserted between GY1SP and the heterologous protein, compared to the Case where GY1SP is directly linked to the heterologous protein.

Example 3

Construction of a Secretory Lipase Expression Plasmid

To express *Candida rugosa*-derived lipase in a plant cell, an expression plasmid was constructed, the plasmid containing a DNA in which a DNA encoding a glycinin signal sequence for endoplasmic reticulum transport and a DNA encoding a lipase has been linked without causing a codon frame shift.

(1) Construction of a Secretory Lipase Expression Plasmid

The nucleotide sequence of SEQ ID NO: 37 was designed based on the amino acid sequence (GenBank Accession Number P20261) of *Candida rugosa*-derived lipase by selecting codons to be matched with plant codon usage, and DNA having the nucleotide sequence was synthesized. The synthesized DNA was inserted between the BamHI site and the HindIII site of the plasmid pTV118N (manufactured Takara Bio Inc.) to obtain plasmid SYN224-78 containing a nucleotide sequence encoding the lipase with modified codons.

Figure 5:
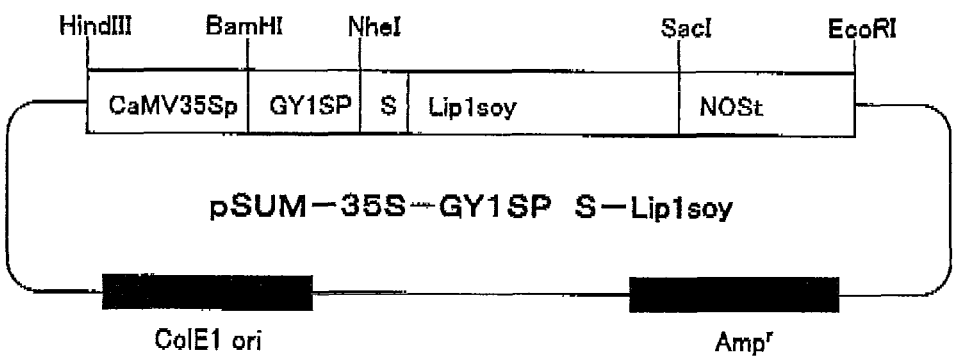
FIG. 5 is a structural schematic diagram of the plasmid pSUM-35S-GY1SP S-Lip1soy.

A PCR was performed by using the plasmid SYN224-78 as a template, and an oligonucleotide consisting of the nucleotide sequence of SEQ ID NO: 38 and an oligonucleotide consisting of the nucleotide sequence of SEQ ID NO: 39 as primers to amplify a DNA fragment having a NheI site and a SacI site respectively at each of the 5'- and 3'-end of the fragment. For the PCR, a DNA polymerase (trade name: KOD-Plus, manufactured by TOYOBO Co., Ltd.) was used and conditions of the reactions were as followed: incubation at 94° C. for 2 minutes, followed by 30 cycles each for 94° C. for 30 seconds, 50° C. for 30 seconds, and 68° C. for 90 seconds; and followed by incubation at 68° C. for 3 minutes. The amplified DNA fragment was purified from the reaction solution by using a DNA fragment purification kit (trade name: MagExtractor-PCR & Gel Clean Up, manufactured by TOYOBO CO., Ltd.), and the purified DNA fragment was ligated by using a gene cloning kit (trade name: TaKaRa BEL Kit, manufactured by TaKaRa Co., Ltd.) to the SmaI site of the plasmid pUC118. The ligation product was introduced into competent cells of *E. coli* DH5α strains (manufactured by TOYOBO Co., Ltd.) and ampicillin resistant strains were selected. Nucleotide sequences of plasmids from the selected resistant strains were analyzed by using a reaction kit for nucleotide sequence analysis (trade name: BigDye Terminator v3.1 Cycle Sequencing Kit, manufactured by Applied Biosystems Japan. Ltd ABI) and a nucleotide sequence analyzer (trade name: ABI Prism 3100 Genetic Analyzer, manufactured by Applied Biosystems Japan. Ltd ABI). A plasmid having an intended nucleotide sequence was digested with NheI and SacI and was obtained a 1.6 kbp DNA fragment encoding a polypeptide in which a serine residue has been fused to the amino terminus of lipase. The lipase-encoding DNA fragment was inserted between the NheI site and the SacI site of the plasmid pSUM-35S-GY1SP S-GFP by replacing the DNA fragment of pSUM-35S-GY1SP S-GFP encoding a fusion protein in which a serine residue has been inserted between GY1SP and GFP with the lipase-encoding DNA fragment to obtain the plasmid pSUM-355-GY1SP S-Liplsoy (FIG. 5) containing the nucleotide sequence of SEQ ID NO: 40 and expressing a fusion protein in which a serine residue has been inserted between GY1SP and lipase.

SEQ ID NO: 37: 5'-

GGATCCATGGCTCCAACTGCAACTCTTGCTAACGGTGATACCATTACTGGACTTAACGCTAT

TATCAATGAGGCATTCCTCGGTATTCCTTTTGCTGAGCCACCTGTTGGTAACCTTAGATTCA

AGGACCCAGTTCCTTACTCCGGATCACTTGATGGTCAGAAGTTTACTTCTTACGGACCATCC

TGCATGCAACAGAATCCAGAAGGTACCTATGAAGAGAACCTCCCAAAGGCTGCACTTGATCT

TGTGATGCAGTCCAAAGTTTTCGAGGCTGTGTCTCCTTCATCCGAGGACTGTCTCACTATTA

ATGTTGTGAGGCCACCTGGAACCAAGGCTGGTGCAAACCTTCCAGTTATGCTTTGGATCTTT

-continued

GGTGGAGGTTTCGAGGTTGGTGGAACTTCAACTTTTCCTCCAGCTCAAATGATCACTAAGTC

TATTGCTATGGGTAAACCAATCATTCATGTTTCAGTGAATTACCGTGTGTCTTCATGGGAT

TCCTCGCAGGTGATGAGATTAAGGCTGAAGGTTCAGCTAACGCTGGACTTAAAGACCAGAGA

CTTGGTATGCAATGGGTTGCAGATAATATTGCTGCTTTTGGAGGTGACCCTACCAAGGTGAC

TATCTTCGGAGAGTCCGCAGGTTCTATGTCTGTTATGTGTCACATTCTTTGGAACGATGGAG

ACAATACTTATAAGGGTAAACCACTCTTCAGAGCTGGAATTATGCAATCTGGTGCTATGGTG

CCTTCAGACGCAGTTGATGGAATCTACGGTAACGAGATTTTTGATCTTCTTGCTTCCAATGC

TGGATGTGGTTCTGCATCCGATAAGCTCGCTTGCCTTAGGGGTGTGTCCTCAGACACACTTG

AAGATGCTACTAACAATACCCCAGGATTCCTCGCATATTCATCTCTTAGACTTTCATACCTT

CCTAGGCCAGACGGTGTTAACATTACAGATGACATGTATGCTCTTGTGAGAGAGGGTAAATA

TGCTAATATCCCTGTTATTATTGGAGATCAGAACGACGAAGGTACTTTCTTCGGAACATCCT

CACTCAATGTGACTACCGACGCTCAGGCAAGAGAGTACTTTAAGCAATCTTTCGTTCATGCT

TCAGATGCAGAAATTGACACTCTTATGACTGCTTATCCAGGTGATATTACTCAAGGCTCCCC

TTTTGACACAGGCATTCTTAACGCTCTCACTCCACAATTCAAGAGGATTTCAGCAGTTCTTG

GCGATCTTGGTTTTACCCTCGCTAGACGTTATTTCCTTAATCATTACACTGGTGGAACAAAG

TATTCTTTCCTTTCAAAACAGCTTTCCGGTCTCCCAGTGCTTGGAACTTTCCACTCAAACGA

CATCGTTTTCCAGGATTATCTTCTCGGTTCCGGTTCTCTTATTTATAATAACGCTTTCATTG

CATTCGCTACCGACCTTGATCCAAATACTGCTGGACTCCTTGTTAAGTGGCCTGAATACACA

TCCTCTTCCCAAAGTGGTAACAACCTTATGATGATCAATGCTCTCGGTCTTTATACTGGTAA

AGACAACTTCAGAACCGCAGGATACGATGCTCTTTTCTCTAATCCTCCATCATTCTTCGTGT

GAGAGCTC-3'

SEQ ID NO: 38: 5'-GCTAGCGCTCCAACTGCAACTCTTGCTAAC-3'

SEQ ID NO: 39: 5'-GAGCTCTCACACGAAGAATGATGGAGGATTAGAG-3'

SEQ ID NO: 40: 5'-

GGATCCATGGCCAAGCTAGTTTTTTCCCTTTGTTTTCTGCTTTTCAGTGGCTGCTGCTTCGC

TAGCGCTCCAACTGCAACTCTTGCTAACGGTGATACCATTACTGGACTTAACGCTATTATCA

ATGAGGCATTCCTCGGTATTCCTTTTGCTGAGCCACCTGTTGGTAACCTTAGATTCAAGGAC

CCAGTTCCTTACTCCGGATCACTTGATGGTCAGAAGTTTACTTCTTACGGACCATCCTGCAT

GCAACAGAATCCAGAAGGTACCTATGAAGAGAACCTCCCAAAGGCTGCACTTGATCTTGTGA

TGCAGTCCAAAGTTTTCGAGGCTGTGTCTCCTTCATCCGAGGACTGTCTCACTATTAATGTT

GTGAGGCCACCTGGAACCAAGGCTGGTGCAAACCTTCCAGTTATGCTTTGGATCTTTGGTGG

AGGTTTCGAGGTTGGTGGAACTTCAACTTTTCCTCCAGCTCAAATGATCACTAAGTCTATTG

CTATGGGTAAACCAATCATTCATGTTTCAGTGAATTACCGTGTGTCTTCATGGGATTCCTC

GCAGGTGATGAGATTAAGGCTGAAGGTTCAGCTAACGCTGGACTTAAAGACCAGAGACTTGG

TATGCAATGGGTTGCAGATAATATTGCTGCTTTTGGAGGTGACCCTACCAAGGTGACTATCT

TCGGAGAGTCCGCAGGTTCTATGTCTGTTATGTGTCACATTCTTTGGAACGATGGAGACAAT

ACTTATAAGGGTAAACCACTCTTCAGAGCTGGAATTATGCAATCTGGTGCTATGGTGCCTTC

AGACGCAGTTGATGGAATCTACGGTAACGAGATTTTTGATCTTCTTGCTTCCAATGCTGGAT

GTGGTTCTGCATCCGATAAGCTCGCTTGCCTTAGGGGTCTGTCCTCAGACACACTTGAAGAT

GCTACTAACAATACCCCAGGATTCCTCGCATATTCATCTCTTAGACTTTCATACCTTCCTAG

```
                               -continued
GCCAGACGGTGTTAACATTACAGATGACATGTATGCTCTTGTGAGAGAGGGTAAATATGCTA

ATATCCCTGTTATTATTGGAGATCAGAACGACGAAGGTACTTTCTTCGGAACATCCTCACTC

AATGTGACTACCGACGCTCAGGCAAGAGAGTACTTTAAGCAATCTTTCGTTCATGCTTCAGA

TGCAGAAATTGACACTCTTATGACTGCTTATCCAGGTGATATTACTCAAGGCTCCCCTTTTG

ACACAGGCATTCTTAACGCTCTCACTCCACAATTCAAGAGGATTTCAGCAGTTCTTGGCGAT

CTTGGTTTTACCCTCGCTAGACGTTATTTCCTTAATCATTACACTGGTGGAACAAAGTATTC

TTTCCTTTCAAAACAGCTTTCCGGTCTCCCAGTGCTTGGAACTTTCCACTCAAACGACATCG

TTTTCCAGGATTATCTTCTCGGTTCCGGTTCTCTTATTTATAATAACGCTTTCATTGCATTC

GCTACCGACCTTGATCCAAATACTGCTGGACTCCTTGTTAAGTGGCCTGAATACACATCCTC

TTCCCAAAGTGGTAACAACCTTATGATGATCAATGCTCTCGGTCTTTATACTGGTAAAGACA

ACTTCAGAACCGCAGGATACGATGCTCTTTTCTCTAATCCTCCATCATTCTTCGTGTGAGAG

CTC-3'
```

(2) Construction of a Cytosolic Lipase Expression Plasmid

Figure 6:
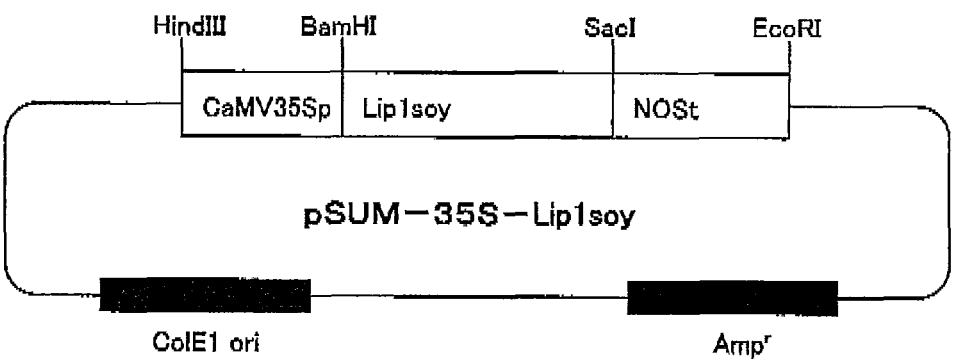
FIG. 6 is a structural schematic diagram of the plasmid pSUM-35 S-Lip1soy.

Plasmid SYN224-78 was digested with BamHI and SacI and a DNA fragment comprising the nucleotide sequence of SEQ ID NO: 37 was purified. The obtained DNA fragment was ligated to plasmid pBI221 digested with BamHI and SacI to obtain plasmid pSUM-35S-Liplsoy (FIG. 6) expressing the lipase to which GY1SP was not linked to.

(3) Construction of a Lipase Expression Binary Vector for Transfection

Figure 7:
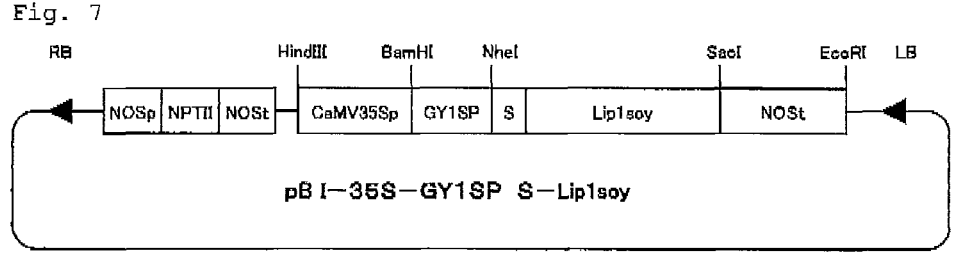
FIG. 7 is a structural schematic diagram of the plasmid pBI-35S-GY1SP S-Lip1soy.
Figure 8:
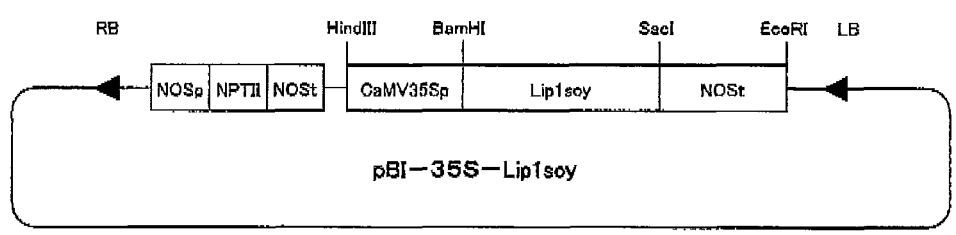
FIG. 8 is a structural schematic diagram of the plasmid pBI-35 S-Lip1soy.

Each of the plasmids obtained in examples 3(1) and (2) was digested with BamHI and SacI to obtain a DNA fragment containing a lipase coding region. Each of the DNA fragments was ligated to the plasmid pBI121 previously-digested with BamHI and SacI, to obtain binary vector plasmid pBI-35S-GY1SP S-Liplsoy (FIG. 7) expressing a fusion protein in which a serine residue has been inserted between GY1SP and lipase, and binary vector plasmid pBI-35S-Liplsoy (FIG. 8) expressing lipase to which GY1SP was not linked to.

(4) Preparation of Anti-Rabbit Lipase Antiserum

Plasmid SYN224-78 was digested with BamHI and SacI to obtain 1.6 kbp-DNA fragment encoding the lipase. The obtained DNA fragment was inserted between BamHI site and HindIII site of plasmid pQE-80L (manufactured by QIAGEN Inc.) to obtain plasmid expressing a lipase to which histidine-tag peptide was linked at the amino-terminal. The expression plasmid was introduced into the *E. coli* JM109 strain and the lipase protein to which histidine-tag peptide has been linked was purified from the obtained transformed *E. coli* strain. A rabbit was immunized by using the purified protein as an antigen and an antiserum (AGC TECHNO GLASS CO., LTO) containing anti-lipase antibody was obtained.

Example 4

Analysis of Expression of Lipase in Recombinant Tobacco (1) Introduction of a Lipase Expression Vector into Tobacco and Selection of Recombinant Tobacco Each of the lipase expression binary vectors prepared in Example 3 (3) was introduced into tobacco through the *Agrobacterium* infection method. The transfection was performed according to the method by Uchimiya (Plant gene manipulation manual. Method for producing transgenic plant, Kodansha Scientific Ltd., 1990, ISBN4-06-153513-7).

Each of lipase expression binary vectors was introduced into *Agrobacterium tumefaciens* LBA4404 (manufactured by Clontech) and the resulting transfected *Agrobacterium* cells were cultured overnight in an LB liquid medium containing 300 mg/L streptomycin, 100 mg/L rifampicin, and 25 mg/L kanamycin. Leaf discs taken from aseptically-cultured tobacco (*Nicotiana tabacum* strain SR-1) were dipped in the overnight culture, planted on MS agar medium (MS inorganic salts, MS vitamins, 3% sucrose, 0.8% agar) with 0.1 mg/L naphthalene acetic acid (NAA) and 1.0 mg/L benzyladenine (SA) added, and then cultured under fluorescent light at 23° C. to 25° C. for 2 days. These cultured leaf discs were washed with sterilized water, and cultured on MS agar medium with 0.1 mg/L NAA, 1.0 mg/L BA, and 500 mg/L cefotaxime added for 7 days to eliminate *Agrobacterium*. Then, the cultured leaf disks were transferred to MS agar medium with 0.1 mg/L NAA, 1.0 mg/L BA, 500 mg/L cefotaxime, and 100 mg/L kanamycin added. The culture of the leaf disks was performed for 2 months by transferring them to fresh medium having the above composition every 2 weeks to induce adventitious budding.

Adventitious buds were transferred to and rooted on MS agar medium with 100 mg/L kanamycin added, to raise them to young plants. The regenerated plants were transferred to potting soil, acclimated to the external environment in a growth chamber, then grown in a greenhouse. After growing the plants in a greenhouse, seeds were harvested.

(2) Lipase Expression Assay of Recombinant Tobacco by Western Blotting Method

Lipase expressed in the recombinant tobacco obtained as described above was detected through western blotting and immunostaining method.

A recombinant tobacco leaf disc of about a 2-cm square was placed in a sampling tube with one zirconia bead (5 mmp, YTZ ball, manufactured by Nikkato Corp.), rapidly frozen under liquid nitrogen, and ground using a grinding apparatus (trade name: Mixermill MM-300, manufactured by Qiagen). After mixing the ground products with 300 μL of PBS buffer, the mixture was centrifuged at 15,000 rpm for 5 minutes at 4° C., the supernatant was collected and centrifuged at 15,000 rpm for 5 minutes at 4° C., and the supernatant was collected. The protein concentration was measured by the method described in Example 2 (2), and lipase protein was detected through SDS-PAGE, western blotting, and immunostaining. As the SDS-PAGE gel (trade name: PAG mini 'Daiichi' manufactured by Daiichi Pure Chemicals Co., Ltd.) was used.

In the antibody reaction of a membrane after the protein transfer, the rabbit antiserum described in Example 3 (4) was used as a primary antibody, and the goat anti-rabbit IgG-AP manufactured by Santa Cruz Biotechnology was used as a secondary antibody. The membrane, after reacting with antibody, was subjected to color-development using the AP kit (manufactured by Bio-Rad) to detect the lipase protein.

As a result of detection through the western blotting, a relatively high level of lipase expression was observed in 15 individuals among 22 individuals of recombinant tobaccos to which pBI-35S-GY1SP S-Lip1soy was introduced, and in 16 individuals among 98 individuals of recombinant tobaccos where pBI-35S-Lip1soy was introduced. T1 seeds obtained from the individuals were seeded on modified MS agar medium containing 50 mg/L kanamycin under aseptic conditions. Then, individuals showing resistance to kanamycin were selected and the selected individuals were grown to obtain T2 seeds. The T2 seeds were seeded again on kanamycin-added media under aseptic conditions, and lines without kanamycin-sensitive individuals were selected as a lipase expression fixed line.

(3) Analysis of Transcription Level of Lipase Gene Through Real-Time PCR

Seeds of selected T2 fixed line were seeded, and a leaf disc of about 2 cm square was sampled after 12 days of acclimation. Total RNA was extracted from the leaf disc by using a plant RNA extraction kit (trade name; RNeasy Plant Mini Kit, manufactured by Qiagen), and cDNA was synthesized from the obtained total RNA by using a cDNA synthesis kit (trade name: ReverTra Ace, manufactured by Toyobo). The quantification of lipase mRNA was performed using the synthesized cDNA as a template, and an oligonucleotide consisting of the nucleotide sequence of SEQ ID No: 41 and an oligonucleotide consisting of the nucleotide sequence of SEQ ID No: 42 as primers, and using a real-time PCR apparatus (trade name: 7500 Fast Real-Time PCR System, manufactured by Applied Biosystems). For an internal standard, the quantity of mRNA of the tobacco ubiquitin gene (GenBank Accession Number U66264) was measured using oligonucleotides consisting of the nucleotide sequences of SEQ ID NOs: 43 and 44 respectively as primers.

Figure 9:
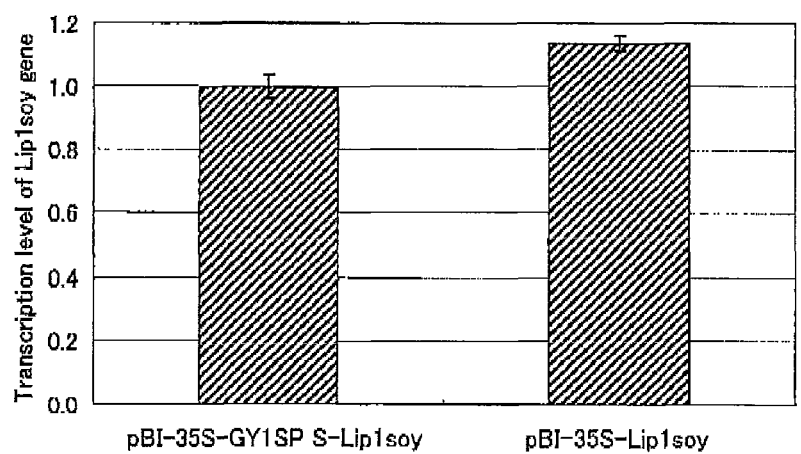
FIG. 9 is a histogram showing transcription level of the lipase gene.

As a result, individuals showing the comparable lipase gene transcription level were obtained in the selected T2 fixed lines to which pBI-35S-GY1SP S-Lip1soy or pBI-35S-Lip1soy has been introduced (FIG. 9).

```
SEQ ID No: 41: 5'-TTGATCTTCTTGCTTCCAATGC-3'

SEQ ID No: 42: 5'-GTCTGAGGACACACCCCTAAGG-3'

SEQ ID No: 43: 5'-GAAGCAGCTCGAGGATGGAA-3'

SEQ ID No: 44: 5'-GACGGGTTGACTCTTTCTGGAT-3'
```

(4) Analysis of Expression Level of Lipase Protein in Recombinant Tobacco

From a leaf disc of the recombinant tobacco individuals having the comparable transcription level of lipase gene, whole cell fraction was fractionated, and extracellular apoplast fraction and cell debris fraction were fractionated according to the method by Boernke et al. (2002, Planta 214, pp. 356-364). Then, the amount of lipase protein was measured in each of the fractions through western blotting and immunostaining method to calculate the amount of secreted lipase protein.

Leaf disks of 0.1 to 0.2 g were taken from each individual after 17 days of acclimation, and proteins were extracted according to the method described in Example 4(2), which was used as a whole cell fraction.

In a similar manner, 5 to 9 g of leafs were taken from each individual after 17 days of acclimation, midribs and to major veins were removed from the leafs, and the leafs were cut into 1 to 2 cm square leaf discs. The leaf discs were infiltrated with 100 mL of 1 M KCl solution under vacuum for 5 minutes. The resulting leaf discs were centrifuged at 1,000 g for 3 minutes at 4° C. and the supernatant was collected, which was used as an extracellular apoplast solution. The solution was further concentrated until the liquid volume was reduced to about ½₀ of the original volume by using centrifugal filter units (trade name: Centriprep YM-10, manufactured by Millipore) and Microcon YM-10, which was used as an extracellular apoplast fraction.

In addition, after the collection of the extracellular apoplast solution, a portion of the precipitate was collected, and then protein was extracted therefrom according to the method described in Example 4(2), which was used as a cell debris fraction. Measurement of protein concentration, SDS-PAGE, and western blotting were performed according to the method described in Example 2(2) for these fractions. ECL Plus Western Blotting Detection Reagent manufactured by GE Health Care was used as a detection reagent for immunostaining method, and a wash buffer solution in which 5% of skim milk was dissolved was used as a blocking solution. In a primary antibody reaction, a solution of the rabbit anti-lipase antiserum described in Example 3(5) diluted 10,000 times with Can Get Signal Immunoreaction Enhancer Solution (manufactured by Toyobo) was used. In a secondary antibody reaction, solutions of ECL Anti-rabbit IgG, Horseradish Peroxidase-Linked Species-Specific Whole Antibody (donkey-derived) manufactured by GE Health Care, and S-protein-HRP conjugate manufactured by GE Health Care diluted 10,000 times and 30,000 times, respectively, with Can Get Signal Immunoreaction Enhancer Solution manufactured by TOYOBO were used. As a standard, Lipase OF (manufactured by Meito Transportation Co., Ltd.) was used.

Figure 10:
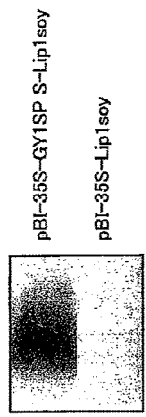
FIG. 10 is an image showing results of detecting lipase protein by Western blot analysis.
Figure 11:
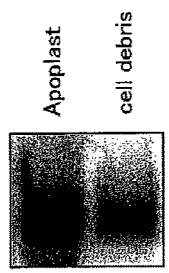
FIG. 11 is an image showing results of detecting lipase protein by Western blot analysis from fractionation of a tobacco in which the plasmid pBI-35S-GY1SP S-Lip1soy has been introduced.

As a result, signal of lipase protein was detected in the recombinant tobacco in which plasmid pBI-35S-GY1SP S-Lip1soy was introduced (FIG. 10). As a result of the fractionation, lipase signal was detected in the extracellular apoplast fraction, indicating the secretion of the lipase protein (FIG. 11). As a result of calculation of the amount of lipase production and the amount of lipase secretion based on the electrophoresis level and the signal intensity of the standard, it was found that 28.9 μg of lipase protein was accumulated for each 1 g wet weight of the leaf, and particularly, 1.76 μg of the lipase was secreted into the extracellular apoplast.

(5) Measurement of Enzyme Activity of Lipase in Recombinant Tobacco Cell Fraction Activity measurement was performed on the fraction, in which lipase protein was detected, by using an enzyme activity measurement reagent (trade name: Lipase Kit 5, manufactured by Dainippon Sumitomo Pharma Co., Led.). As a standard, Lipase OF (manufactured by Meito Transportation Co., Ltd.) was used.

As a result, it was found that, in the recombinant tobacco in which plasmid pBI-35S-GY15P S-Lip1soy was introduced, the activities of the whole cell fraction and the extracellular apoplast fraction were 5.7 IU and 37.3 IU, respectively, for each 1 g of total protein. According to the above described results, it was found that the recombinant tobacco in which the plasmid pBI-35S-GY15P S-Lip1soy was introduced produced enzymatically-active lipase and secreted the enzymatically-active lipase to the extracellular apoplast region.

Furthermore, it is supposed that the lipase secreted to the extracellular apoplast region has high activity and folding and processing is performed accurately.

Example 5

Construction of a Lipase Secretory Expression Plasmid Containing Glycinin Gene Promoter and Terminator To express *Candida rugosa*-derived lipase in a plant seed, was constructed seed-specific expression plasmid in which glycinin gene promoter and terminator were operably linked to DNA encoding an intended protein.

A PCR was performed by using the plasmid pSUM-GY1 disclosed in European Patent application 0571741 as a template, an oligonucleotide consisting of the nucleotide sequence of SEQ ID NO 45 and an oligonucleotide consisting of the nucleotide sequence of SEQ ID NO: 46 as primers to amplify a glycinin gene promoter fragment having a BamHI site at 3'-end of the fragment. For the PCR, a DNA polymerase (trade name: KOD-Plus, manufactured by TOYOBO Co., Ltd.) was used and conditions of the reactions were as followed: incubation at 94° C. for 2 minutes, followed by 25 cycles each for 94° C. for 30 seconds, 40° C. for 30 seconds, and 68° C. for 2 minutes; and followed by incubation at 68° C. for 3 minutes. The amplified DNA fragment obtained was ligated to PCR product insertion site of the plasmid pCR2.1-TOPO (trade name, manufactured by Invitrogen Inc.).

In a similar manner, PCR was performed with an oligonucleotide consisting of the nucleotide sequence of SEQ ID NO: 47 and an oligonucleotide consisting of the nucleotide sequence of SEQ ID NO: 48 as primers to amplify a glycinin gene terminator fragment having a SacI site and a HindIII site respectively at each of the 5'- and 3'-end of the fragment. The amplified DNA fragment was ligated between the SacI site and the HindIII site of the plasmid into which the glycinin gene promoter fragment has been inserted.

Terminally-phosphorylated synthetic oligonucleotides with the nucleotide sequences of SEQ ID NOs:49 and 50 respectively were mixed at an equivalent mole ratio, heated at 65° C. for 5 minutes, and then cooled slowly to prepare a linker. The prepared linker was inserted between the BamHI site and the SadI site of the plasmid into which the glycinin gene promoter fragment and the glycinin gene terminator fragment have been inserted. The resulting plasmid was digested with EcoRI and HindIII and was inserted into plasmid pUC19 (Takara bio Inc.).

The ligation product was introduced into competent cells (Toyobo Inc.) of the *E. coli* DH5α strain ampicillin resistant strains were selected. Nucleotide sequence of plasmid of the selected ampicillin resistant strain was analyzed by using the nucleotide sequence analysis reaction kit, BigDye Terminator v3.1 Cycle Sequencing Kit (Applied Biosystem Inc.) and the nucleotide sequence analyzer, ABI Prism 3100 Genetic Analyzer (Applied Biosystems Inc.) to obtain plasmid having glycinin gene promoter and terminator.

Figure 12:
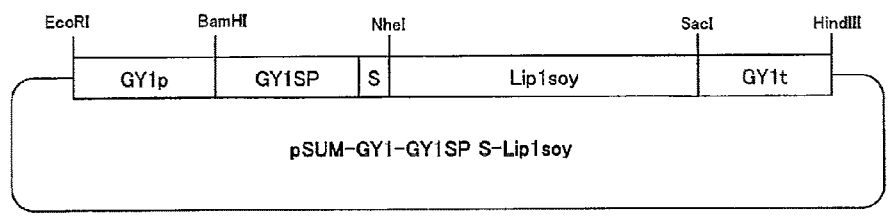
FIG. 12 is a structural schematic diagram of the plasmid pSUM-GY1-GY1SP S-Lip1soy.

The linker having the glycinin signal sequence for ER transport prepared in Example 1 (1), and 1.6 kpb DNA fragment encoding a polypeptide in which a serine residue has been fused to the amino terminus of lipase prepared in Example 3(1) were inserted between the BamHI site and the SacI site of the plasmid having glycinin gene promoter and terminator. Thus, was obtained plasmid pSUM-GY1-GY1SP S-Liplsoy (FIG. 12) containing the nucleotide sequence of SEQ ID NO: 51, containing glycinin gene promoter and terminator, and expressing a fusion protein in which a serine residue has been inserted between GY1SP and lipase.

```
SEQ ID NO: 45: gttttcccagtcacgac

SEQ ID NO: 46: ggatccGACTGATGAGTGTTTAAGGACCAATG

SEQ ID NO: 47: gagctcAACCAATAAATAATAATAATAATG

SEQ ID NO: 48: aagcttCAAGTCATGAAGAACCTGATAAGACGTC

SEQ ID NO: 49: gatccgcggccgcgagct

SEQ ID NO: 50: cgcggccgcg

SEQ ID NO: 51: 5'- gaattcTCTCTTATAAAACACAAACACAATTTTTAGATTTTATTTAAATAATCATCAATCGA

TTATAATTATTTATATATTTTTCTATTTTCAAAGAAGTAAATCATGAGCTTTTCCAACTCAA

CATCTATTTTTTTTCTCTCAACCTTTTTCACATCTTAAGTAGTCTCACCCTTTATATATATA

ACTTATTTCTTACCTTTTACATTATGTAACTTTTATCACCAAAACCAACAACTTTAAAATTT

TATTAAATAGACTCCACAAGTAACTTGACACTCTTACATTCATCGACATTAACTTTTATCTG

TTTTATAAATATTATTGTGATATAATTTAATCAAAATAACCACAAACTTTCATAAAAGGTTC

TTATTAAGCATGGCATTTAATAAGCAAAAACAACTCAATCACTTTCATATAGGAGGTAGCCT

AAGTACGTACTCAAAATGCCAACAAATAAAAAAAAAGTTGCTTTAATAATGCCAAAACAAAT

TAATAAAACACTTACAACACCGGATTTTTTTAATTAAAATGTGCCATTTAGGATAAATAGT

TAATATTTTTAATAATTATTTAAAAAGCCGTATCTACTAAAATGATTTTTATTTGGTTGAAA

ATATTAATATGTTTAAATCAACACAATCTATCAAAATTAAACTAAAAAAAAAATAAGTGTAC

GTGGTTAACATTAGTACAGTAATATAAGAGGAAAATGAGAAATTAAGAAATTGAAAGCGAGT
```

-continued

```
CTAATTTTTAAATTATGAACCTGCATATATAAAAGGAAAGAAAGAATCCAGGAAGAAAAGAA
ATGAAACCATGCATGGTCCCCTCGTCATCACGAGTTTCTGCCATTTGCAATAGAAACACTGA
AACACCTTTCTCTTTGTCACTTAATTGAGATGCCGAAGCCACCTCACACCATGAACTTCATG
AGGTGTAGCACCCAAGGCTTCCATAGCCATGCATACTGAAGAATGTCTCAAGCTCAGCACCC
TACTTCTGTGACGTGTCCCTCATTCACCTTCCTCTCTTCCCTATAAATAACCACGCCTCAGG
TTCTCCGCTTCACAACTCAAACATTCTCTCCATTGGTCCTTAAACACTCATCAGTCggatcc
ATGGCCAAGCTAGTTTTTTCCCTTTGTTTTCTGCTTTTCAGTGGCTGCTGCTTCGCTAGCGC
TCCAACTGCAACTCTTGCTAACGGTGATACCATTACTGGACTTAACGCTATTATCAATGAGG
CATTCCTCGGTATTCCTTTTGCTGAGCCACCTGTTGGTAACCTTAGATTCAAGGACCCAGTT
CCTTACTCCGGATCACTTGATGGTCAGAAGTTTACTTCTTACGGACCATCCTGCATGCAACA
GAATCCAGAAGGTACCTATGAAGAGAACCTCCCAAAGGCTGCACTTGATCTTGTGATGCAGT
CCAAAGTTTTCGAGGCTGTGTCTCCTTCATCCGAGGACTGTCTCACTATTAATGTTGTGAGG
CCACCTGGAACCAAGGCTGGTGCAAACCTTCCAGTTATGCTTTGGATCTTTGGTGGAGGTTT
CGAGGTTGGTGGAACTTCAACTTTTCCTCCAGCTCAAATGATCACTAAGTCTATTGCTATGG
GTAAACCAATCATTCATGTTTCAGTGAATTACCGTGTGTCTTCATGGGGATTCCTCGCAGGT
GATGAGATTAAGGCTGAAGGTTCAGCTAACGCTGGACTTAAAGACCAGAGACTTGGTATGCA
ATGGGTTGCAGATAATATTGCTGCTTTTGGAGGTGACCCTACCAAGGTGACTATCTTCGGAG
AGTCCGCAGGTTCTATGTCTGTTATGTGTCACATTCTTTGGAACGATGGAGACAATACTTAT
AAGGGTAAACCACTCTTCAGAGCTGGAATTATGCAATCTGGTGCTATGGTGCCTTCAGACGC
AGTTGATGGAATCTACGGTAACGAGATTTTTGATCTTCTTGCTTCCAATGCTGGATGTGGTT
CTGCATCCGATAAGCTCGCTTGCCTTAGGGGTGTGTCCTCAGACACACTTGAAGATGCTACT
AACAATACCCCAGGATTCCTCGCATATTCATCTCTTAGACTTTCATACCTTCCTAGGCCAGA
CGGTGTTAACATTACAGATGACATGTATGCTCTTGTGAGAGAGGGTAAATATGCTAATATCC
CTGTTATTATTGGAGATCAGAACGACGAAGGTACTTTCTTCGGAACATCCTCACTCAATGTG
ACTACCGACGCTCAGGCAAGAGAGTACTTTAAGCAATCTTTCGTTCATGCTTCAGATGCAGA
AATTGACACTCTTATGACTGCTTATCCAGGTGATATTACTCAAGGCTCCCCTTTTGACACAG
GCATTCTTAACGCTCTCACTCCACAATTCAAGAGGATTTCAGCAGTTCTTGGCGATCTTGGT
TTTACCCTCGCTAGACGTTATTTCCTTAATCATTACACTGGTGGAACAAAGTATTCTTTCCT
TTCAAAACAGCTTTCCGGTCTCCCAGTGCTTGGAACTTTCCACTCAAACGACATCGTTTTCC
AGGATTATCTTCTCGGTTCCGGTTCTCTTATTTATAATAACGCTTTCATTGCATTCGCTACC
GACCTTGATCCAAATACTGCTGGACTCCTTGTTAAGTGGCCTGAATACACATCCTCTTCCCA
AAGTGGTAACAACCTTATGATGATCAATGCTCTCGGTCTTTATACTGGTAAAGACAACTTCA
GAACCGCAGGATACGATGCTCTTTTCTCTAATCCTCCATCATTCTTCGTGTGAgagctcAAC
CAATAAATAATAATAATAATGAATAAGAAAACAAAGGCTTTAGCTTGCCTTTTGTTCAC
TGTAAAATAATAATGTAAGTACTCTCTATAATGAGTCACGAAACTTTTGCGGGAATAAAAGG
AGAAATTCCAATGAGTTTTCTGTCAAATCTTCTTTTGTCTCTCTCTCTCTCTTTTTTTTT
TCTTTCTTCTGAGCTTCTTGCAAAACAAAAGGCAAACAATAACGATTGGTCCAATGATAGTT
AGCTTGATCGATGATATCTTTAGGAAGTGTTGGCAGGACAGGACATGATGTAGAAGACTAAA
ATTGAAAGTATTGCAGACCCAATAGTTGAAGATTAACTTTAAGAATGAAGACGTCTTATCAG
GTTCTTCATGACTTG-3'
```

Example 6

Analysis of Lipase Expression in Recombinant Soybean Seed (1) Introduction of a Lipase Expression Vector into a Soybean and Selection of Recombinant Soybean Lipase expression plasmids prepared in Example 3 (1) and Example 5 respectively were introduced into soybean spherical somatic embryo by the particle gun method, and the introduction of the lipase genes into the selected spherical somatic embryo was identified through PCR.

A hypocotyl segment of an immature embryo extracted from sterilized soybean immature seed was cut into two immature cotyledons. Then, the immature cotyledons were placed in induction medium (MS inorganic salts, B5 media vitamins (Gamborg at al., Exp. Cell Res. (1968) Vol. 50, pp. 151-158), 180 µM 2,4-D, 3% sucrose, 0.2% gel-lyte, pH 7.0), and cultured at a temperature 23° C. to 25° C. for approximately 1 month (at 23 hours light and 1 hour dark conditions everyday). The thus-formed spherical somatic embryos were transplanted to proliferation medium (MS inorganic salts, B5 media vitamins, 90 µM 2,4-D, 3% sucrose, 0.2% gel-lyte, pH 5.8), and then transplanted again to a fresh medium having the same composition every 2 or 3 weeks to perform culture 5 to 8 times under the same conditions.

Each of lipase expression plasmids prepared in Example 3 (1) and Example 5 was mixed with the same amount of a plasmid in which DNA (GenBank Accession number: V01499) encoding *E. coli*-derived APH4 has been linked downstream to the promoter of plasmid pG8CRG1-2 described in U.S. Pat. No. 6,218,598, and was introduced into the spherical somatic embryos cultured for 3 to 4 days in a fresh proliferation medium by using a gene transfer apparatus (trade name: PDS-1000/He system, manufactured by Bio-Rad). Three (3) to 4 days after the introduction treatment, the embryos were transferred to selection medium (MS inorganic salts, B5 media vitamins, 30 µM hygromycin, 90 µm 2,4-D, 3% sucrose, pH 5.8) solidified with 0.2% gel-lyte or liquid selection medium, and cultured at a temperature 23° C. to 25° C. at 23 hours light and 1 hour dark conditions. The embryos were transferred to a fresh medium having the same composition every 2 or 3 weeks to perform culturing 5 to 8 times under the same condition. Further, in the case of the liquid selection medium, rotary culture was performed at 100 rpm.

The selected spherical somatic embryos were sampled, 40 µL of a nucleic acid extraction reagent (trade name: PrepMan Ultra Reagent, manufactured by Applied Biosystems) was added to the embryos, and heated to 100° C. for 10 minutes. After cooling, centrifugation was performed at 15,000 rpm and 22° C. for 1 minute and the supernatant was collected, which was used as a genomic DNA solution. PCR was performed using the extracted genomic DNA solution as a template, and an oligonucleotide consisting of the nucleotide sequence of SEQ ID No: 52 and an oligonucleotide consisting of the nucleotide sequence of SEQ ID No: 53 as primers, and spherical somatic embryos in which lipase genes have been introduced were selected. For the PCR, a DNA polymerase (trade name: TaKaRa Ex Taq Hot Start Version, manufactured by Takara Bio Inc.) was used and conditions of the reactions were as follows: incubation at 94° C. for 2 minutes, followed by 30 cycles each for 94° C. for 30 seconds, 55° C. for 30 seconds, and 72° C. for minutes; and followed by incubation at 72° C. for 2 minutes.

SEQ ID NO:52: ctggtgcaaaccttccagtt
SEQ ID NO:53: ttatcggatgcagaaccaca

The selected recombinant spherical somatic embryos were transplanted to emersion medium (MS inorganic salts, B5 media vitamins, 3% sucrose, 0.2% gel-lyte, pH 5.8), cultured for 6 to 8 weeks, and then dried for 1 to 2 weeks. The somatic embryos which became white to yellow cotyledon-shaped embryos were transferred to germination medium (MS inorganic salts, 55 media vitamins, 3% sucrose, 0.2% gel-lyte, pH 5.8) and cultured for 2 weeks. The regenerated individuals rooted and developed true leaves were transferred to potting soil and acclimated in a growth chamber. After growing the individuals in a greenhouse, seeds were harvested.

(2) Analysis of Expression Amount of Lipase Protein in Recombinant Soybean Seed by Western Blotting Method Proteins were extracted from recombinant soybean seed and was quantified by Western blotting method and the immunostaining method to calculate the production amount of lipase protein.

The recombinant soybean seed which was allowed to absorb water overnight was divided into four pieces, and each piece was put in a tube containing one zirconia bead (5 mmφ, YTZ ball) (manufactured by Nikkato Corp.), and was rapidly frozen under liquid nitrogen. The frozen seeds were ground by using a grinding apparatus (trade name: Mixermill MM-300, manufactured by QIAGEN gmbh.), mixed with PBS buffer with being added by 300 µL by using the mixer mill, and centrifuged at 15,000 rpm, 4° C. for 5 minutes to collect supernatant. The collected supernatant was centrifuged at 15,000 rpm for 5 minutes at 4° C., and the supernatant was collected. The concentration of protein was measured by the method described in Example 2(2), and then SDS-PAGE, Western blot and immunostaining were performed. In the primary antibody reaction, solution obtained by diluting 50,000 times the rabbit anti-lipase antiserum described in Example 3(5) with Can Get Signal Immunoreaction Enhancer Solution (manufactured by Toyobo Inc.) was used, and in the secondary antibody reaction, solution obtained by diluting ECL Anti-rabbit IgG, Horseradish Peroxidase-Linked Species-Specific Whole Antibody (donkey-derived) (manufactured by GE health care Inc.) and S-protein-HRP conjugate (manufactured by GE health care Inc.) 50,000 times with Can Get Signal Immunoreaction Enhancer Solution (manufactured by Toyobo Inc.) was used. The lipase OF (manufactured by Meito Industry Inc.) was used as a standard.

Figure 13:
FIG. 13 is an image showing results of detecting lipase protein by Western blot analysis.

As a result, a signal of lipase protein was detected from the recombinant soybean seed to which the plasmid pSUM-GY1-GY1SP S-Liplsoy has been introduced (FIG. 13). The production amount of lipase was calculated based on the mobility on electrophoresis and a signal intensity of the standard, and it was found that lipase protein corresponding to about 0.5% of soluble protein was produced.

(3) Analysis of Amino-Terminal Amino Acid Sequence of Lipase in Recombinant Soybean Seed Ammonium sulphate was added by 30% to protein extract of the recombinant soybean seed from which the signal of lipase protein was detected, mixed, and centrifuged at 15,000 rpm, 4° C. for 20 minutes. PBS buffer was added to the obtained precipitates and mixed to measure the protein concentration and perform the Western blot analysis by the method disclosed in Example 2(2). A membrane onto which protein was transferred was shaked for 10 minutes by using staining solution (0.1% CBB, 50% methanol, 10% acetic acid), was destained twice by using destaiing solution (50% methanol, 10% acetic acid), and was washed twice by using washing solution. A band detected at a position of about 60 kDa was cut and provided for the analysis of amino-terminal amino acid sequence.

As a result, the amino acid sequence of SEQ ID NO: 54, which is a serine residue followed by an amino acid sequence of lipase, was detected, and it was found that the expressed fusion protein was processed immediately downstream of the glycinin signal sequence for ER transport.

SEQ ID NO:54: SAPTA (4) Measurement of Enzyme Activity of Lipase in Protein Extract of a Recombinant Soybean Seed A measurement of enzyme activity was performed on protein extract of a recombinant soybean seed in which lipase proteins were detected. Substrate 4-Nitrophenyl decanoate manufactured by SIGMA Co. Ltd. was dissolved in DMSO and the mixture was added into 50 mM potassium phosphate buffer (pH 6.50) containing 0.5% Triton X-100 manufactured by Nacalai Tesque, Inc. to prepare a 2.5 mM dilution as a substrate solution, 30 μL of protein extract of a recombinant soybean seed in which a plasmid pSUM-GY1-GY1SP S-Lip1soy was introduced was mixed with 370 μL of 2.5 mM substrate solution to perform a reaction at 30° C. for 10 minutes. Acetone of 800 μL was added and mixed as a reaction stop solution. The resulting reaction solution was centrifuged at 15,000 rpm for 1 minute at 22° C., and the optical density of 1 mL supernatant was measured at 410 nm. 4-nitrophenol manufactured by Fluke Co. Ltd. was used as a standard. In addition, 1U is defined as the amount of an enzyme to produce 1 μmol of 4-nitrophenol as a hydrolysate of the substrate per minute.

As a result, it could be seen that a recombinant soybean seed in which the plasmid pSUM-GY1-GY1SP 5-Lip1soy has been introduced had 17.8 U of lipase activity per gram of dry seed weight. From these results, it was apparent that a recombinant soybean seed in which the plasmid pSUM-GY1-GY1SP S-Liplsoy has been introduced accumulated lipase having enzyme activity.

What is claimed is:

1. A method for producing a heterologous protein secreted out of a plant cell, said method comprising:
introducing into a plant cell genome a DNA encoding an amino acid sequence that comprises a glycinin signal sequence for endoplasmic reticulum transport and an amino acid sequence of a heterologous protein, wherein one amino acid is inserted between the signal sequence and the amino acid sequence of the heterologous protein, and wherein the one amino acid is serine; and
expressing the DNA.

2. The method according to claim 1, wherein the glycinin signal sequence for endoplasmic reticulum transport is the amino acid sequence of SEQ ID NO:1.

3. A method for producing a transgenic plant cell secreting a heterologous protein, said method comprising:
introducing into a plant cell genome a DNA encoding an amino acid sequence that comprises a glycinin signal sequence for endoplasmic reticulum transport and an amino acid sequence of a heterologous protein, wherein one amino acid is inserted between the signal sequence and the amino acid sequence of the heterologous protein, and wherein the one amino acid is serine.

4. A plant expression plasmid comprising a DNA encoding an amino acid sequence that comprises a glycinin signal sequence for endoplasmic reticulum transport and an amino acid sequence of a heterologous protein, wherein one amino acid is inserted between the signal sequence and the amino acid sequence of the heterologous protein, and wherein the one amino acid is serine.

5. A DNA encoding an amino acid sequence that comprises a glycinin signal sequence for endoplasmic reticulum transport and an amino acid sequence of a heterologous protein, wherein one amino acid is inserted between the signal sequence and the amino acid sequence of the heterologous protein, and wherein the one amino acid is serine.

6. A plant cell with a genome into which a DNA encoding an amino acid sequence is introduced, the amino acid sequence comprising a glycinin signal sequence for endoplasmic reticulum transport and an amino acid sequence of a heterologous protein, wherein one amino acid is inserted between the signal sequence and the amino acid sequence of the heterologous protein, and wherein the one amino acid is serine.

7. A plant with a genome into which a DNA encoding an amino acid sequence is introduced, the amino acid sequence comprising a glycinin signal sequence for endoplasmic reticulum transport and an amino acid sequence of a heterologous protein, wherein one amino acid is inserted between the signal sequence and the amino acid sequence of the heterologous protein, or a seed of the plant, and wherein the one amino acid is serine.

8. The method according to claim 1, further comprising a step of recovering the heterologous protein secreted out of the plant cell.

9. The plant expression plasmid according to claim 4, wherein the heterologous protein is a green fluorescent protein (GFP).

* * * * *